United States Patent [19]
Martel et al.

[11] 3,962,223
[45] June 8, 1976

[54] SUBSTITUTED CEPHENE-4-CARBOXYLATES AND THEIR METHOD OF PREPARATION

[75] Inventors: Jacques Martel, Bondy; Rene Heymes, Romainville, both of France

[73] Assignee: Roussel-UCLAF, Paris, France

[22] Filed: Jan. 2, 1973

[21] Appl. No.: 320,493

[30] Foreign Application Priority Data

Dec. 31, 1971 France .............................. 71.47758
Dec. 31, 1971 France .............................. 71.47759
Dec. 31, 1971 France .............................. 71.47760
Dec. 31, 1971 France .............................. 71.47761
Dec. 31, 1971 France .............................. 71.47762
Dec. 31, 1971 France .............................. 71.31699

[52] U.S. Cl. .......................... 260/243 C; 424/246
[51] Int. Cl.² .............. C07D 501/06; C07D 501/22; C07D 501/29
[58] Field of Search ............................... 260/243 C

[56] References Cited
UNITED STATES PATENTS

| | | |
|---|---|---|
| 3,634,417 | 1/1972 | Attenburrow .................. 260/243 C |
| 3,655,656 | 4/1972 | Van Heyman, Jr. ............ 260/243 C |
| 3,769,280 | 10/1973 | Parker ............................ 260/243 C |
| 3,828,037 | 8/1974 | De Marinis et a. ............. 260/243 C |

*Primary Examiner*—Raymond V. Rush
*Assistant Examiner*—James H. Turnipseed
*Attorney, Agent, or Firm*—Hammond & Littell

[57] ABSTRACT

Novel desacetoxycephalosporin derivatives of the formula

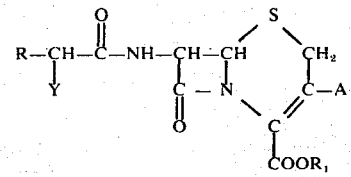

in racemic or optically active form or cis and trans forms and mixtures thereof wherein R is selected from the group consisting of aminophenyl and R', R' is selected from the group consisting of phenyl optionally substituted with at least one member of the group consisting of halogen and nitro and a 5 to 6 member heterocyclic group, Y is selected from the group consisting of amino, NHCOOR" where R" is alkyl of 1 to 5 carbon atoms, hydrogen and hydroxy, A is selected from the group consisting of alkyl of 2 to 5 carbon atoms and cycloalkyl of 3 to 7 carbon atoms optionally containing a heteroatom and $R_1$ is selected from the group consisting of hydrogen, easily acid hydrolyzable group and easily hydrogenolysis removable group, with the proviso that when R is aminophenyl Y is other than amino and NHCOOR" and $R_1$ is hydrogen and when Y is amino, $R_1$ is hydrogen and the non-toxic pharmaceutically acceptable addition salts of with organic and inorganic bases and acids where appropriate which have antibacterial activity and a novel process for their preparation and novel intermediates therefor.

8 Claims, No Drawings

SUBSTITUTED CEPHENE-4-CARBOXYLATES AND THEIR METHOD OF PREPARATION

OBJECTS OF THE INVENTION

It is an object of the invention to provide the novel desacetoxycephalosporin compounds of formula I and the salts thereof.

It is another object of the invention to provide a novel process for the preparation of compounds of formula I and novel intermediates produced thereby.

It is an additional object of the invention to provide novel antibacterial compositions.

It is a further object of the invention to provide a novel method of combatting bacterial infections in warmblooded animals.

These and other objects and advantages of the invention will become obvious from the following detailed description.

The novel products of the invention are desacetoxycephalosporin derivatives selected from the group consisting of racemates and optically active isomers of cis and trans forms and mixtures thereof compounds of the formula

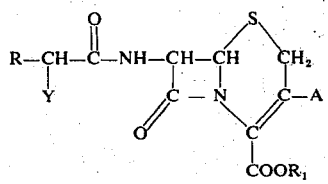

wherein R is selected from the group consisting of aminophenyl and R', R' is selected from the group consisting of phenyl optionally substituted with at least one member of the group consisting of halogen and nitro and a 5 to 6 member heterocyclic group, Y is selected from the group consisting of amino, NHCOOR'' where R'' is alkyl of 1 to 5 carbon atoms, hydrogen and hydroxy, A is selected from the group consisting of an alkyl of 2 to 5 carbon atoms and cycloalkyl of 3 to 7 carbon atoms optionally containing a heteroatom and $R_1$ is selected from the group consisting of hydrogen, easily acid hydrolyzable group and easily hydrogenolysis removable group, with the proviso that when R is aminophenyl, Y is other than amino and NHCOOR'' and $R_1$ is hydrogen and when Y is amino, $R_1$ is hydrogen and the non-toxic, pharmaceutically acceptable addition salts of with organic and inorganic bases and acids where appropriate.

In the compounds of formula I, R' may be nitrophenyl, halophenyl, dihalophenyl or phenyl and a heterocyclic such as thienyl or pyridyl. $R_1$ may be hydrogen, alkyl of 1 to 6 carbon atoms such as methyl, ethyl, propyl, isopropyl, butyl, isobutyl, and tert.-butyl optionally substituted with at least one halogen such as trichloroethyl or aralkyl of 7 to 15 carbon atoms such as benzyl and p-methoxybenzyl. A may be alkyl of 2 to 5 carbon atoms such as ethyl, propyl, isopropyl, butyl, isobutyl, or tert.-butyl or cycloalkyl of 3 to 7 carbon atoms which may contain a heteroatom such as oxygen or sulfur as cyclopentyl.

In a preferred group of compounds of formula I and their salts, R is phenyl, p-nitrophenyl, p-aminophenyl or 2-thienyl, Y is hydrogen or amino, A is ethyl, isopropyl or cyclopentyl and $R_1$ is hydrogen and in another group, R is phenyl, p-nitrophenyl or 2-thienyl, Y is hydrogen or —NHCOO— tert.-butyl, A is ethyl, isopropyl or cyclopentyl and $R_1$ is tert.-butyl.

Examples of suitable non-toxic, pharmaceutically acceptable bases for the addition salts are mineral bases such as sodium, or potassium hydroxide, potassium carbonate and organic bases such as cyclohexylamine, triethylamine, diphenylenediamine or dibenzyl ethylenediamine. Examples of suitable acids for the addition salts are mineral acids such as hydrogen halides, sulfuric acid, phosphoric acid, nitric acid and boric acid and organic acids such as formic acid, acetic acid, benzoic acid, salicyclic acid and p-toluene sulfonic acid.

The process for the preparation of compounds within formula I having the formula

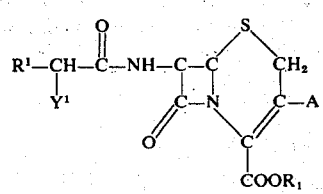

wherein $R_1$ and A have the above definition and $R^1$ is selected from the group consisting of phenyl optionally substituted with at least one halogen or nitro and a 5 to 6 heterocyclic and $Y^1$ is selected from the group consisting of NHCOOR'', hydrogen and hydroxy and $R^1$ is alkyl of 1 to 5 carbon atoms comprises reacting a compound of the formula

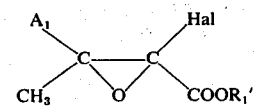

wherein $A_1$ is selected from the group consisting of methyl and A, $R_1'$ is selected from the group consisting of easily hydrolyzable and easily hydrogenatable removable groups and Hal is selected from the group consisting of chlorine and bromine with a dehydrohalogenating agent to form an ester of an α-methylene-α-oxo-carboxylic acid of the formula

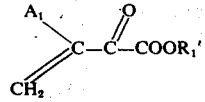

reacting the said ester in the presence of a weakly basic tertiary amine with a threo isomer, erythro isomer or mixtures thereof of a thioaminal of the formula

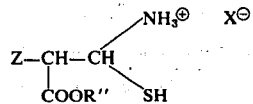

wherein Z is selected from the group consisting of optionally substituted cyclic imido, benzoylamino and thiobenzoylamino, $R_1''$ is selected from the group consisting of alkyl of 1 to 10 carbon atoms and aralkyl of 7 to 15 carbon atoms and X is an anion selected from the group consisting of halogen, sulfuric and sulfonic to either form a 1,3-thiazine of the formula

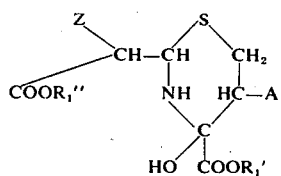  VI existing in threo or erythro form or a mixture thereof, subjecting the latter to hydrogenolysis or hydrazine treatment and then to an acid to obtain a 2,3-dihydro-1,3-thiazine of the formula

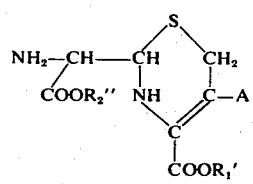  VII or to form a 1,3-thiazine of the formula

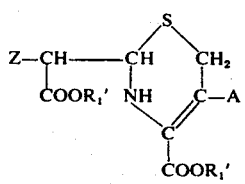  VI' existing in threo or erythro form or mixtures thereof, subjecting the latter to hydrazine or hydrogenolysis to obtain the compound of formula VII, subjecting the latter to selective saponification with a basic agent to obtain a compound of the formula

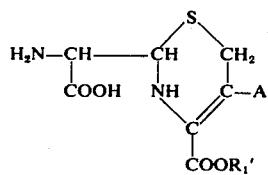  VIII in its threo or erythro form or a mixture thereof, reacting the latter with a tritylating agent to form a 2,3-dihydro-1,3-thiazine of the formula

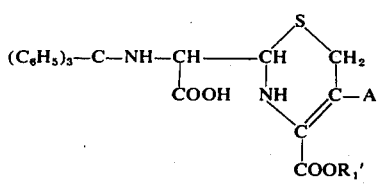  IX in its threo or erythro form or mixtures thereof, subjecting the latter to cyclization with a lactamization agent to form a compound of the formula

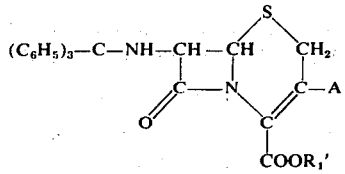  X in its cis or transform or mixtures thereof and either reacting the latter with an acid under mild conditions to form a compound of the formula

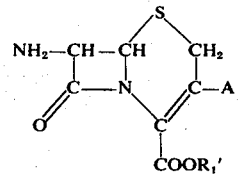  XI in its cis or transform and mixtures thereof or reacting the compound of formula X with an acid agent under severe conditions to form a compound of the formula

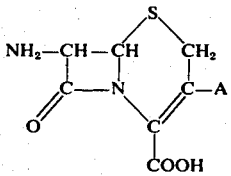  XIa in its cis or transform or mixtures thereof. The compound of formula XI can be reacted with an acid hydrolysis agent or subjected to hydrogenolysis to form the free acid of formula XIa. The compounds of formula XI or XIa may be treated with a resolution agent to form the optically active isomer, if desired.

The compound of formula XI can also be reacted with a compound of the formula $$R^1\text{---}CH\text{---}COOH \quad \text{XII}$$
$$\phantom{R^1\text{---}CH}Y^1$$

or a reactive derivative thereof to form a compound of the formula

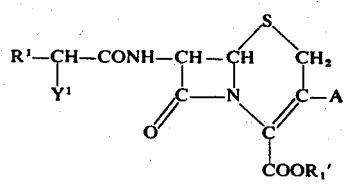  IIa which can be subjected to acid hydrolysis or hydrogenolysis to form the corresponding free acid of the formula

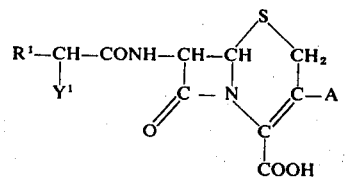  IIb

The compounds of formula XIa may also be reacted with a compound of the formula

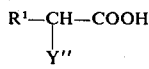
                        XIII or a functional derivative thereof wherein Y'' is H or —OH to form a compound of formula IIb which may be reacted with a base to form the corresponding non-toxic, pharmaceutically acceptable addition salt.

The compounds of formula IV have an important industrial interest as they are intermediates useful in the synthesis of cephalosporin type compounds. Processes are known for obtaining compounds analogous to formula IV [Vogel, Helv., Vol. 33 (1950), p. 125] but the processes are commerically difficult in the lack of selectivity and in poor yields. The process of the invention, however, gives good yields and is selective.

The dehydrohalogenation of the compound of formula III is preferably effected with lithium bromide or silver nitrate but other lithium and silver salts such as lithium chloride, lithium acetate, silver acetate or silver perchlorate may be used or trimethylmine salt of 0,0-dimethyl dithiophosphate or a Lewis acid such as boron trifluoride or aluminum chloride may also be used. The reaction is effected in an organic solvent, especially a good solvent for the products present such as hexamethylphosphorotriamide, dimethylsulfoxide, dimethylformamide, acetonitrile, acetone or tetrahydrofuran.

The starting products of formula III can be made by a method analogous to Darzens [C.R. Acad. Sci., Vol. 151 (1910), p. 203 and 883]. The product of formula IV may be made by the process of British Patent No. 1,101,961.

The weakly basic tertiary amine for the condensation of the compounds of formula V and IV is pyridine or triethylamine and is effected in the presence of other tertiary amines, especially quinolein, picoline or collidine.

In the compounds of formula VI and VIa wherein Z is an optionally substituted cyclic imido group, the splitting off the Z group is preferably effected by an exchange function with hydrazine and when Z is benzoylamino or thiobenzoylamino, it is effected by hydrogenolysis in the presence of a platinum or palladium catalyst. In this case it is equally possible to effect an alkylation of the ketone or thioketone function at the first step with an alkyl sulfate or a Meerwein reactant to obtain the corresponding imino ether or imino thio ether which is then hydrolyzed with a mineral or organic acid such as acetic acid or dilute hydrochloric acid.

The transformation of compound VI into compound VII is terminated by acid treatment of the dehydration of an intermediate product formed and not isolated of the formula

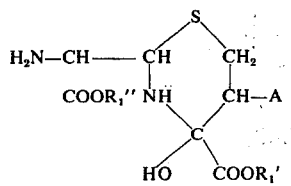

to form a compound of formula VII. Preferably, hydrochloric acid is used but other mineral acids such as sulfuric acid or hydrobromic acid as well as organic acids such as p-toluenesulfonic acid and trifluoroacetic acid may be used.

The basic agent used to saponify the $COOR''_1$ group is preferably sodium hydroxide but also useful are potassium hydroxide, lithium hydroxide, alkali metal carbonates such as sodium carbonate or potassium carbonate and the reaction is effected in the cold.

The thioaminals of formula V may be prepared by the process of French Patent No. 2,130,800 consisting of treating an enamine of the formula

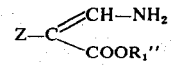
                        XIV with hydrogen sulfide in the presence of a hydrohalide acid and the enamines of formula XIV may be prepared by the process of French Pat. No. 1,469,529.

The tritylation agent for reaction with a compound of formula VIII is trityl chloride and the reaction is effected in the presence of an alkaline agent, preferably a tertiary amine such as trimethylamine, triethylamine, N-methylpiperidine, pyridine, N-methylpyrrolidine or quinolein.

The preferred lactamization agent is a dialkyl or dicycloalkylcarbodiimide such as dicyclohexylcarbodiimide or diisopropylcarbodiimide and the reaction is effected in a polar solvent such as nitromethane, disubstituted amide, a sulfoxide, acetone or acetonitrile and in the presence of a tertiary amine such as pyridine, collidine or a dialkylaniline. The medium may also contain an additional solvent such as methylene chloride or chloroform.

The acid agent for the mild treatment of compounds of formula X may be a mineral or organic acid such as dilute hydrochloric acid or acetic acid and is effected in an organic solvent such as nitromethane, chloroform, methylene chloride or methanol. The reaction of a compound of formula XI to form a compound of formula XIa is preferably with a reducing agent as hydrogenolysis agent such as a zinc-acetic acid system and hydrochloric acid as the acid hydrolysis agent particularly admixed with acetic acid. In a preferred made, trifluoroacetic acid is the acid hydrolysis agent.

The acid agent for the severe treatment of compounds of formula X to form a compound of formula XIa is preferably hydrogen chloride gas, hydrofluoric acid or trifluoroacetic acid and is effected in an organic solvent such as nitromethane, chloroform, methylene chloride or methanol.

The resolution of the compounds of formula XI and XIa is effected with an optically active organic carboxylic or sulfonic acid such as tartaric acid, dibenzoyltartaric acid, camposulfonic acid or glutamic acid and decomposition of the salt is effected with a mineral base such as sodium bicarbonate or an organic amine such as tertiary amines like triethylamine.

The acids of formula XII are preferably in the form of their functional derivatives such as the acid chloride or acid anhydride formed in situ by action of dicyclohexylcarbodiimide with the acid. Equally useful are the halides or other amides formed insitu by action with dialkylcarbodiimide or dicycloalkylcarbodiimides as well as other acid derivatives such as acid azide, acid amide or acid ester.

If the compound of formula XI is reacted with a halide of the acid of formula XII, the reaction is preferably effected in the presence of a basic agent such as alkali metal carbonates, trialkylamine or pyridine.

The reaction of a compound of formula II to one of formula IIb is effected with an acid hydrolysis agent such as hydrochloric acid alone or mixed with acetic acid and with a hydrogenolysis agent such as a reducing agent with a zinc-acetic acid system. Preferably, a hydrolysis agent and more preferably trifluoroacetic acid is used.

The compounds coming within the scope of formula I and having the formula

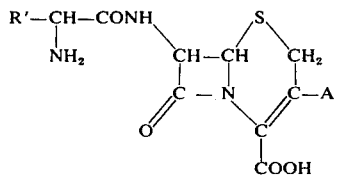
                                            IIc or their esters or salts may be prepared by subjecting a compound of the formula

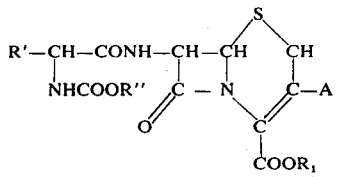
                                            XV to an acid hydrolyzing agent or to hydrogenolysis to form the desired product of formula IIc which may be esterified or salified. The acid hydrolysis agent is preferably hydrochloric acid admixed with acetic acid and the hydrogenolysis is effected with a zinc-acetic acid system as the reducing agent. A preferred acid hydrolysis agent is trifluenoacetic acid.

Compounds with formula I having the formula

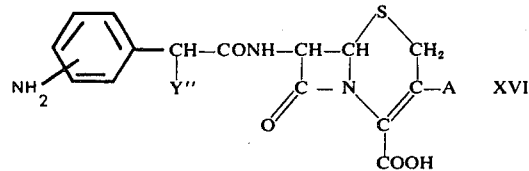
                                            XVI or their salts or esters may be prepared by reacting a compound of the formula

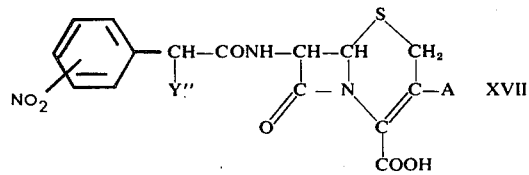
                                            XVII with a reducing agent to form the compound of formula XVI which may be esterified or salified. The reduction is preferably effected with hydrogen in presence of a catalyst based on a platinum group metal such as palladium, preferably fixed on an inert support such as carbon, alkaline earth metal sulfate, alkaline earth carbonate, alumina, magnesium or talc. The estification may be effected by known methods such as reaction with an alcohol in the presence of an acid agent.

Among the novel intermediate products of the invention are tert.-butyl 3-methyl-2-oxo-3-butenoate, tert.-butyl 3-isopropyl-2-oxo-3-butenoate, compounds of formula IX, and X, compounds of the formula

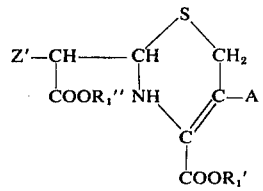

wherein $Z'$ is amino or Z and Z, A, $R_1'$ and $R_1''$ have the above meaning and compounds of the formula

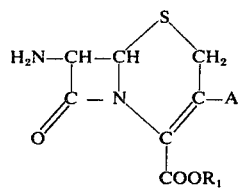

wherein $R_1$ and A have the above definitions and their salts.

The novel antibacterial compositions of the invention are comprised of an effective amount of a compound of formula I or a salt thereof and a pharmaceutical carrier. The compositions may be in the form of injectable solutions or suspensions, sterile powders for extemporaneous injectable preparations, tablets, coated tablets, capsuls, syrups, suppositaries, creams, pomades and cerosals prepared in the usual manner.

The compositions due to their antibacterial activity are useful for the treatment of staphylococci such as septicemia of staphylococcus, malignant staphylococci of the face, cutaneous staphylococcus, pyodermitis, septic sores and suppurate, anthrax, phlegm, eresypeles, primitive acute staphylococci or post grippe, bronchopneumonia and pulmonary suppurations. For example, L(+) cis 7-[D(−)-α-aminophenylacetamido]-3-3thyl (or cyclopentyl)-3-cepheme-4-carboxylic acid is active against gram positive bacteria such as staphylococci and staplococci and particularly penicillin resistant staphylococci and certain gram negative bacteria, particularly coliform bacteria.

The novel method of the invention for combatting bacterial infections in warm-blooded animals including man comprises administering an antibacterially effective amount of a compound of formula I or a non-toxic, pharmaceutically acceptable addition salt there to the warm-blooded animal. The compound may be administered orally, rectally, parenterally or locally by topical application to the skin or mucus membranes. The usual daily dose is to mg/kg depending upon the compound and made of administration.

In the following examples there are described several preferred embodiments to illustrate the invention. However, it should be understood that the invention is not to be limited to the specific embodiments.

EXAMPLE 1

Tert.-butyl 3-METHYL-2-oxo-3-butenoate

STEP A: tert-butyl 2-chloro-2,3-epoxy-3-methyl-butanoate

A solution of 70.8 g of potassium tert.-butylate in 500 ml of tetrahydrofuran was added over 30 minutes under an inert atmosphere to 111 g of tert.-butyl dichloroacetate and 35.5 g of acetone at 0°C and after letting the mixture return to room temperature, the mixture was stirred for 1 hour and poured into iced water. The mixture was extracted with petroleum ether and the extract was washed twice with water and dried over sodium sulfate. 40 g of alumina were added thereto and after stirring, the mixture was filtered to remove mineral products. The solvent was removed from the filtrate by distillation under reduced pressure to obtain 116.5 g of tert.-butyl 2-chloro-2,3-epoxy-3-methyl-butanoate in the form of a colorless liquid soluble in the usual organic solvents and insoluble in water.

I.R. Spectrum: C=O at $1743^{cm-1}$

STEP B: tert.-butyl 3-methyl-2-oxo-3-butenoate 97 g of silver nitrate and 200 ml of water were added with stirring at 20°C to a solution of 116.5 g of tert.-butyl 2-chloro-2,3-epoxy-3-methyl-butanoate in 1.16 liters of acetone, and after standing at room temperature for 2 hours, the silver chloride precipitate formed was removed by filtration. The filtrate was washed with water and extracted with petroleum ether. The organic phase was washed twice with water and was dried over sodium sulfate. 40 g of alumina were added thereto with stirring and the mineral products were removed by filtration. The solvent was distilled off at reduced pressures below 40°C to obtain 81.7 g of tert.-butyl 3-methyl-2-oxo-3-butenoate in the form of a clear yellow liquid soluble in the usual organic solvents and insoluble in water.

U.V. Spectrum (ethanol): Max. at 224 m$\mu$ $E_{1cm}^{1\%}$ = 261

EXAMPLE 2

Tert.-butyl 3-isopropyl-2-oxo-3-butenoate

STEP A: tert.-butyl 2-chloro-2,3-epoxy-3-isopropyl-butanoate

A solution of 122 g of potassium tert.-butylate in 720 ml of tetrahydrofuran was added with stirring under an inert atmosphere at −20°C to a mixture of 95 g of methyl isopropyl ketone and 185 g of tert.-butyl dichloroacetate and the mixture was allowed to return to room temperature and was stirred for 2 hours. The mixture was poured into iced water and stirred after which the organic phase was removed, washed with aqueous sodium chloride solution and dried over magnesium sulfate. After passing the solution through vegetable black, the solution was concentrated to dryness to obtain 230.4 g of tert.-butyl 2-chloro-2,3-epoxy-3-isopropyl-butanoate in the form of a colorless liquid soluble in the usual organic solvents and insoluble in water.

| Analysis: | $C_{11}H_{19}O_3Cl$; | molecular weight = 234.725 | |
|---|---|---|---|
| Calculated: | %C 56.29 | %H 8.16 | %Cl 15.10 |
| Found: | 56.2 | 8.3 | 15.6 |

I.R. Spectrum: C=O at $1748^{cm-1}$ and absorption region C—O—C

STEP B: Tert.-butyl 3-isopropyl-2-oxo-3-butenoate 118 g of anhydrous lithium bromide were added under a nitrogen atmosphere at 5°C to a mixture of 117.5 g of tert.-butyl 2-chloro-2,3-epoxy-3-isopropyl-butanoate in 18.5 g of lithium carbonate and 1.15 liters of hexamethylphosphortriamide and after returning to room temperature, the mixture was stirred under a nitrogen atmosphere for 48 hours. 500 ml of distilled water were added thereto and the mixture was added to a decanting flask containing a 9:1 mixture of water and petroleum ether. After decanting, the aqueous phase was extracted with petroleum ether and the combined organic phases were washed with water, dried over magnesium sulfate, then the petroleum ether was evaporated under reduced pressure to obtain 84.6 g of tert.-butyl 3-isopropyl-2-oxo-3-butenoate in the form of a yellow liquid soluble in the usual organic solvents and insoluble in water.

U.V. Spectrum (ethanol): Max. at 225 m$\mu$ $E_{1cm}^{1\%}$ = 302; $\epsilon$ = 6000

EXAMPLE 3

Threo isomer of 2-($\alpha$-carboxy-$\alpha$-aminomethyl)-4-tert.-butoxycarbonyl-5-ethyl-2,3-dihydro-1,3-thiazine STEP A: 3-ethyl-2-hydroxy-3-butenenitrile A mixture of 42 g of 2-ethyl-2-propenal (described by Grenn, J. Chem. Soc., 1957, p. 3262), 50 ml of dimethylformamide and 65 ml of acetic acid were added all at once under a nitrogen atmosphere to a solution of 49 g of sodium cyanide in 100 ml of dimethylformamide cooled to −10°C and the mixture was then stirred at room temperature for 3 hours. 600 ml of isopropyl ether were added thereto and the mixture was vacuum filtered to remove the sodium acetate precipitate formed. The filter was washed with isopropyl ether and the ether phase was washed with water and dried over magnesium sulfate. The solvent was evaporated off under reduced pressure to obtain 53 g of 3-ethyl-2-hydroxy-butenenitrile in the form of a pale yellow oil soluble in ether and methylene chloride and slightly soluble in water.

I.R. Spectrum: OH band at $3579^{cm-1}$ and C=C at $1,651^{cm-1}$

STEP B: ETHYL 3-ethyl-2-hydroxy-3-butenoate

A mixture of 31 g of 3-ethyl-2-hydroxy-3-butenenitrile and 35 ml of ethanol saturated with hydrochloric acid was held at 0°C for 1 hour and the precipitate formed was empasted with 350 ml of ether. The mixture was vacuum filtered and the filter was washed with ether to obtain 9.7 g of product. The product was dried and then was dissolved in 20 ml of water. The solution was stirred for 1 hour at room temperature and then sodium chloride was added thereto until the aqueous phase was saturated. The mixture was extracted with ether and the ether phase was dried over magnesium sulfate and evaporated to dryness under reduced pressure to obtain 7.8 g of ethyl 3-ethyl-2-hydroxy-3-butenoate in the form of a colorless liquid soluble in ether, methylene chloride and alcohols and slightly soluble in water.

I.R. Spectrum: Ester at $1728^{cm-1}$, C=C at $1651^{cm-1}$ and OH band at $3591^{cm-1}$ STEP C: ethyl 3-ethyl-2-oxo-3-butenoate 16 g of magnesium dioxide were added to a solution of 3.2 g of ethyl 3-ethyl-2-hydroxy-3-butenoate in 65 ml of methylene chloride and the mixture was stirred at room temperature for 1½ hours. and was filtered. The solvent was distilled from the filtrate under reduced pressure to obtain ethyl 3-ethyl-2-oxo-3-butenoate in the form of a colorless liquid soluble in ether and alcohols and slighly soluble in water.

U.V. Spectrum (ethanol): Max. at 225 nm $E_{1cm}^{1\%} = 494$

STEP D: tert.-butyl 3-ethyl-2-oxo-3-butenoate 95 ml of 2N aqueous sodium hydroxide were added over 1 hour to a solution of 33 g of ethyl 3-ethyl-2-oxo-3-butenoate in 360 ml of a 9:1 mixture of dioxane and water and after the addition, the solvents were evaporated off. The crystallized residue was taken up in dioxane and the solution was vacuum filtered. The product was dried under reduced pressure until the weight was constant and the 39.5 g of product were added to 700 ml of condensed isobutylene. 14 ml of concentrated sulfuric acid were added thereto under a nitrogen atmosphere at −50°C and the mixture was stirred in an air tight enclosure overnight at room temperature. After evaporation of excess butylene, the mixture was added to methylene chloride and excess sulfuric acid was neutralized by addition of aqueous sodium hydroxide. The mixture was extracted with methylene chloride and the organic phase was washed with water and dried over magnesium sulfate. The solvent was evaporated at below 30°C to obtain 41 g of tert.butyl 3-ethyl-2-oxo-3-butenoate in the form of a clear yellow oil soluble in ether, ethanol and benzene and slightly soluble in water.

U.V. Spectrum (ethanol): Max. at 225 nm $E_{1cm}^{1\%} = 287$

STEP E: Thioaminal of methyl phthalimidomalonalaldehydate .HCl 12 g of hydrogen sulfide, 8 g of gaseous hydrochloric acid and 50 g of methyl 2-phthalimido-3-amino-acrylate (prepared by process of French Pat. No. 1,469,529) were dissolved in 400 ml of nitromethane cooled to −10°C, and after standing for 2 hours at room temperature, the cold solution was vacuum filtered. The precipitate recovered was washed with a 50—50 nitromethane-ether mixture, then with ether and then dried to obtain a first yield of 17.1 g of the thero isomer of the thioaminal of methyl phthalimidomalonalaldehydate hydrochloride. The filtrate after standing 3 hours gave a second yield of 3.6 g of said product. The solution was then cooled to −10°C, and after the addition of 4 g of gaseous hydrochloric acid and 6 g of hydrogen sulfide the mixture was allowed to stand overnight to obtain a third yield of 18.6 g of the said product. Finally, the solution yielded a fourth crop of 3.2 g of the product after standing for 3 days for a total yield of 42.5 g. The product occurred in the form of colorless crystals melting at 180°C with decomposition and soluble in water, slightly soluble in ethanol and methanol and insoluble in ether and chloroform.

STEP F: Threo isomer of 2-(α-methoxycarbonyl-α-phthalimidomethyl-4-tert.-butoxycarbonyl-5-ethyl-2,3-dihydro1,3-thiazine 6.65 ml of pyridine were added at −10°C to a mixture of 11.35 g of tert.-butyl 3-ethyl-2-oxo-3-butenoate, 4.55 ml of ethanol and 26 g of the thioaminal of methyl phthalimidomalonalaldehydate hydrochloride and the mixture was stirred for 3 hours while allowing the temperature to rise to room temperature. 26 ml of water were added thereto and after cooling at 0°C for 1 hour, the mixture was vacuum filtered. The recovered precipitate was washed with a 20% aqueous ethanol solution and dried at 50° under reduced pressure to obtain 18.85 g of the threo isomer of 2-(α-methoxycarbonyl-α-phthalimidomethyl)-4-tert.-butoxycarbonyl-5-ethyl-2,3-dihydro1,3-thiazine in the form of yellow crystals melting at 140° − 142°C. The product was soluble in methylene chloride, slightly soluble in ethanol and insoluble in water.

| Analysis: | $C_{22}H_{26}O_6N_2S$; | molecular weight = 446.51 | | |
|---|---|---|---|---|
| Calculated: | %C 59.18 | %H 5.87 | %N 6.27 | %S 7.18 |
| Found: | 58.9 | 5.6 | 6.2 | 6.9 |

I.R. Spectrum (chloroform): Presence of phthalimido at 1776 and $1721^{cm-1}$, conjugated ester at $1721^{cm-1}$ and of ester β of a nitrogen at $1748^{cm-1}$.

| U.V. Spectrum (ethanol): | | |
|---|---|---|
| Max. at 217 nm | $E^{1\%}_{1cm} = 971$ | $\epsilon = 43,500$ |
| Inflex. towards 238 nm | $E^{1\%}_{1cm} = 271$ | |
| Max. at 290 nm | $E^{1\%}_{1cm} = 122$ | $\epsilon = 5,400$ |

STEP G: Threo isomer of 2-(α-methoxycarbonyl-α-aminomethyl) -4-tert.butoxycarbonyl-5-ethyl-2,3dihydro-1,3-thiazine 4.46 g of 2-(α-methoxycarbonyl-α-phthalimidomethyl) -4-tert.-butoxycarbonyl-5-ethyl-2,3-dihydro-1,3-thiazine (threo isomer) were added at 0 to 5°C to 5.5 ml of a solution of 2M hydrazine hydrate in dimethylformamide and after stirring the mixture at room temperature for 30 minutes, 50 ml of ether and 3 ml of acetic acid were added thereto. After standing for 45 minutes, the mixture was vacuum filtered and the product recovered was washed with ether. The combined ether phases were washed with an aqueous saturated sodium bicarbonate solution, then with water, dried over magnesium sulfate and evaportated to dryness to obtain 3.3 g of the threo isomer of 2-(α-methoxycarbonyl-α-aminomethyl)-4-tert.butoxycarbonyl-5-ethyl-2,3-dihydro-1,3-thiazine.

STEP H: Threo isomer of 2-(α-carboxy-α-aminomethyl)-4-tert.butyoxycarbonyl-5-ethyl-2,3-dihydro-1,3-thiazine The product of Step G was dissolved at 0°C in 10 ml of acetone and then 10 ml of N sodium hydroxide were added thereto with stirring under a nitrogen atmosphere. After standing for 15 minutes, another 0.75 ml of acetic acid were added thereto and agitation at room temperature was continued for 30 minutes. The mixture was vacuum filtered and the recovered precipitate was washed with a 50—50 acetone-water mixture, then with acetone and dried at 40°C under reduced pressure to obtain 1.715 g of the threo isomer of 2-(α-carboxyα-aminomethyl)-4-tert.-butoxycarbonyl-5-ethyl-2,3-dihydro-1,3-thiazine with a melting point greater than 190°C. The product occurred in the form of ocre crystals slightly soluble in water, acetone and ethanol.

| Analysis: | $C_{13}H_{22}O_4N_2S$; | molecular weight = 302.40 | | |
|---|---|---|---|---|
| Calculated: | %C 51.60 | %H 7.33 | %N 9.27 | %S 10.60 |
| Found: | 51.4 | 7.2 | 9.1 | 10.7 |

I.R. Spectrum (Nujol): Absorption region OH/NH, presence of carbonyl at 1733 and 1715$^{cm-1}$.

U.V. Spectrum (ethanol): Max. at 280 nm $E_{1cm}^{1\%}$ = 107

EXAMPLE 4

Threo isomer of 2-(α-carboxy-α-aminomethyl)-4-tert.-butoxycarbonyl-5-isopropyl-2,3-dihydro-1,3-thiazine STEP A: Threo and erythro isomers of 2-(α-methoxycarbonyl-α-phthalimidomethyl)-4-tert.-butoxycarbonyl-5-isopropyl-2,3-dihydro-1,3-thiazine 95 g of the thioaminal of methyl phthalimidomalonalaldehydate hydrochloride (threo and erythro isomers) were added to a solution of 84.4 of tert.-butyl 3-isopropyl-2-oxo-3-butenoate in 420 ml of ethanol cooled to −20°C and then 66 ml of an ethanol solution of 40 ml of pyridine per 100 ml of ethanolic solution were added thereto while holding a −20°C temperature. The mixture was allowed to stand at room temperature for 2 hours and then 80 ml of water were added thereto. The mixture was cooled in an ice bath for 45 minutes and was then vacuum filtered. The precipitate was washed with a 1—1 water-ethanol solution and was then empasted with petroleum ether and dried to obtain 108.1 g of threo and erythro isomers of 2-(α-methoxycarbonyl-α-phthalimidomethyl)-4-tert.butoxycarbonyl-5-isopropyl-2,3-dihydro-1,3-thiazine which was used as is for the next step.

STEP B: Threo and erythro isomers of 2-(α-methoxycarbonyl-α-aminomethyl)-4-tert.-butoxycarbonyl-5-isopropyl-2,3-dihydro-1,3-thiazine 55 ml of a solution of 2M hydrazine hydrate in dimethylformamide were added with stirring under a nitrogen atmosphere to a solution of 46.1 g of the product from Step A in 461 ml of chloroform cooled to 0°C and the mixture was stirred for 1 hour at room temperature. 600 ml of ether and 30 ml of acetic acid were added thereto and the mixture, after standing for 1 hour, was filtered. The filter was washed with ether and the filtrate was added to 400 ml of aqueous saturated sodium bicarbonate solutions. The mixture was stirred for 10 minutes and was then decanted. The organic phase was washed with water and the wash waters were extracted with ether. The combined organic phases were dried over magnesium sulfate and the solvent was evaporated off under reduced pressure to obtain threo and erythro isometric mixture of 2-(α-methoxycarbonyl-α-aminomethyl)-4-tert.-butoxycarbonyl-5-isopropyl-2,3-dihydro-1,3-thiazine.

STEP C: Threo isomer of 2-(α-carboxyα-aminomethyl)-4-tert.butoxycarbonyl-5-isopropyl-2,3-dihydro-1,3-thiazine The product of Step B was dissolved under a nitrogen atmosphere with stirring in 100 ml of acetone and the 100 ml of N sodium hydroxide was added to the solution cooled at 0°C. The mixture stood for 20 minutes and then 6.3 ml of acetic acid were added thereto and the mixture was stirred for 1 hour. The mixture was vacuum filtered and the precipitate was empasted with ether, vacuum filtered and dried under reduced pressure. The dried residue was ground, empasted with acetone, then ether and dried under reduced pressure to obtain 13.2 g of the threo isomer of 2-(α-carboxy-α-aminomethyl)-4-tert.-butoxycarbonyl-5-isopropyl-2,3-dihydro-1,3-thiazine melting at 150°C with decomposition. The product occurred in the form of yellowish white crystals slightly soluble in water and ethanol and insoluble in ether.

| Analysis: | $C_{14}H_{24}O_4N_2S$; | | molecular weight = 316.42 | |
|---|---|---|---|---|
| Calculated: | %C 53.15 | %H 7.65 | %N 8.86 | %S 10.12 |
| Found: | 52.9 | 7.6 | 9.2 | 9.9 |

U.V. Spectrum (ethanol): Max. at 280–281 nm $E_{1cm}^{1\%}$ = 90 ∊=2900

I.R. Spectrum (Nujol): Absorption area OH/NH, C=O at 1729 $cm^{-}$ and absorption towards 1698—1679-$cm^{-}$.

EXAMPLE 5

Tert.-butyl DL cis 7-tritylamino-3-ethyl-3-cepheme-4-carboxylate

STEP A: threo isomer of 2-(α-carboxy-α-tritylaminomethyl)-4-tert.-butoxycarbonyl-5-ethyl-2,3-dihydro-1,3-thiazine A solution of 30.8 g of trityl chloride in 150 ml of chloroform was added to a solution of 30.24 g of the threo isomer of 2-(α-carboxy-α-aminomethyl)-4-tert.-butoxycarbonyl5-ethyl-2,3-dihydro-1,3-thiazine in 300 ml of chloroform and 30.8 ml of triethylamine cooled at −50°C and after letting the mixture stand for 45 minutes at −50°C, the temperature was returned to room temperature. The mixture was filtered to remove in solubles and the solvents were evaporated off under reduced pressure. The residue was taken up in 450 ml of methanol and 48.5 ml of 2N hydrochloric acid were added thereto under nitrogen with stirring. After cooling to 0°C. the mixture was stirred for 45 minutes and was vacuum filtered. The precipitate was washed with methanol containing 10% water then with methanol and dried at 50°C under reduced pressure to obtain 45.6 g of the threo isomer of 2-(α-carboxy-α-tritylaminomethyl)-4-tert.-butoxycarbonyl-5-ethyl-2,3-dihydro-1,3-thiazine melting at 200°C with decomposition. The product occurred in the form of ocre crystals slightly soluble in methanol and insoluble in water.

| Analysis: | $C_{32}H_{36}O_4N_2S.0.25\ CH_3OH$; | | molecular weight = 552.63 | |
|---|---|---|---|---|
| Calculated: | %C 70.1 | %H 6.75 | %N 5.07 | %S 5.79 |
| Found: | 70.0 | 6.6 | 5.3 | 6.1 |

I.R. Spectrum (Nujol): Presence of NH at 3356 and 3320$^{cm-1}$, conjugated ester C=O at 1715$^{cm-1}$, acid C=O at 1686$^{cm-1}$ and aromatic C=C at 1628, 1594 and 1401$^{cm-1}$ U.V. Spectrum (ethanol):
| | |
|---|---|
| Inflex. towards 228 nm | $E^{1\%}_{1cm}$ = 262 |
| Max. at 263 nm | $E^{1\%}_{1cm}$ = 54 |
| Max. at 272 nm | $E^{1\%}_{1cm}$ = 56 |
| Max. at 286 nm | $E^{1\%}_{1cm}$ = 59    ∊ = 3200 |

STEP B: Tert.-butyl DL cis 7-tritylamino-3-ethyl-3-cepheme-4-carboxylate

A solution of 19.3 g of dicyclohexylcarbodiimide in 193 ml of chloroform was added to a mixture of 43.5 g of the threo isomer of Step A in 2200 ml of nitromethane and after the mixture stood for 1 hour at room temperature, 120 ml of pyridine were added thereto. After standing at room temperature for 4 hours, the mixture was vacuum filtered and the filter was washed with nitromethane. The filtrate was evaporated to dryness under reduced pressure and the residue was taken up in a 1-1 ether-methylene chloride mixture. The insolubles were removed by vacuum filtration and the filtrate was evaporated to dryness. The residue was dissolved in 100 ml of methanol and the solutions was cooled at 0°C for 1 hour and vacuum filtered. The precipitate obtained was washed with methanol and then was dried under reduced pressure to obtain 25.4 g of tert.-butyl DL cis 7-tritylamino-3-ethyl-3-cepheme-4-carboxylate melting at 178°C. The product occurred in the form of cream crystals soluble in chloroform and ehthanol, slightly soluble in methanol and insoluble in water.

| Analysis: | $C_{32}H_{34}O_3N_2S$; | | molecular weight = 526.61 | |
|---|---|---|---|---|
| Calculated: | %C 72.98 | %H 6.51 | %N 5.32 | %S 6.08 |
| Found: | 73.3 | 6.6 | 5.4 | 5.9 |

I.R. Spectrum (chloroform): Presence of β-lactam at $1776^{cm-1}$, conjugated ester at $1714^{cm-1}$, aromatic bands C=C at 1636, 1598 and $1488^{cm-1}$ and NH at $3342^{cm-1}$ U.V. Spectrum (ethanol):
Inflex. towards 26 nm      $E^{1\%}_{1cm} = 302$
Max. at 262 nm             $E^{1\%}_{1cm} = 120$     $\epsilon = 6300$

EXAMPLE 6

Tert.-butyl DL cis 7-tritylamino-3-isopropyl-3-cepheme-4-carboxylate

STEP A: Threo isomer of 2-(α-carboxy-α-tritylaminomethyl)-4-tert.-butoxycarbonyl-5-isopropyl-2,3-dihydro-1,3-thiazine A solution of 10.7 g of tritylchloride in 70 ml of chloroform was added with stirring under a nitrogen atmosphere to a solution of 11.1 g of the threo isomer of 2-(α-carboxy-α-aminomethyl)-4-tert.butoxycarbonyl-5-isopropyl-2,3-dihydro1,3-thiazine in 140 ml of chloroform and 10.8 ml of triethylamine cooled to −50°C after standing at −50°C for 30 minutes, the temperature was raised to room temperature. The mixture was evaporated to dryness and the residue was dissolved in 170 ml of methanol. 21.5 ml of 2N hydrochloric acid were added thereto and after stirring at 0°C for 15 minutes, the mixture was vacuum filtered. The precipitate was washed with methanol and then ether and was dried to obtain 9.1 g of the threo isomer of 2-(α-carboxy-α-tritylaminomethyl)-4-tert.butoxycarbonyl-5-isopropyl-2,3-dihydro-1,3-thiazine melting at 180°C with decomposition. The product occurred in the form of colorless crystals soluble in chloroform, slightly soluble in ethanol and insoluble in water.

| Analysis: | $C_{33}H_{38}O_4N_2S$; | | molecular weight = 558.75 | |
|---|---|---|---|---|
| Calculated: | %C 70.94 | %H 6.86 | %N 5.01 | %S 5.73 |
| Found: | 71.0 | 6.7 | 4.8 | 5.9 |

I.R. Spectrum (Nujol): Presence of C=O, free and associated NH and aromatic bands U.V. Spectrum (ethanol + dioxane):
Inflex. towards 227 nm     $E^{1\%}_{1cm} = 269$
Max. at 264 nm             $E^{1\%}_{1cm} = 55$
Max. at 273 nm             $E^{1\%}_{1cm} = 55$
Max. at 287 nm             $E^{1\%}_{1cm} = 56$     $\epsilon = 3,130$ STEP B: Tert.-butyl dl cis 7-tritylamino-3-isopropyl-3-cepheme-4-carboxylate A solution of 6.4 g of dicyclohexylcarbodiimide in 52 ml of chloroform was added to a mixture of 14.9 g of the product of Step A in 15 ml of chloroform and 1500 ml of nitromethane cooled to 0°C and after returning the temperature to room temperature, 27 ml of pyridine were added to the mixture which was stirred for 15 hours under a nitrogen atmosphere. The insolubles were removed by vacuum filtration and after rinsing the filter with ether, the combined filtrates were evaporated to dryness. The residue was dissolved in 60 ml of methylene chloride and the solution was vacuum filtered again. The filtrate was evaporated to dryness and the residue was suspended in 95 ml of ethanol. The mixture was stirred at room temperature for 15 minutes and then for 15 minutes after cooling. The mixture was vacuum filtered and the recovered precipitate was washed with ethanol, then with petroleum ether and dried to obtain 8.3 g tert.-butyl DL cis 7-tritylamino-3-isopropyl-3-cepheme-4-carboxylate.

For analysis, 13.6 gm of the product were added to 41 ml of methylene chloride and the solution was filtered. 200 ml of ethanol were added to the filtrate and the mixture was concentrated to a small volume and was vacuum filtered. The precipitate was washed with ethanol and then with petroleum ether and dried to obtain 12.5 g of pure product melting at 227°C. The product occurred in the form of colorless crystals soluble in chloroform, slightly soluble in ethanol and insoluble in water.

| Analysis: | $C_{33}H_{36}O_3N_2S$; | | molecular weight = 540.74 | |
|---|---|---|---|---|
| Calculated: | %C 73.31 | %H 6.71 | %N 5.18 | %S 5.92 |
| Found: | 73.1 | 6.7 | 5.1 | 5.7 |

I.R. Spectrum (chloroform): Presence of β-lactam at $1773^{cm-1}$, conjugated ester at $1721^{cm-1}$, aromatics and C=C at 1653, 1616 and $1597^{cm-1}$.

U.V. Spectrum (ethanol):
Inflex. towards 228 nm     $E^{1\%}_{1cm} = 297$
Max. at 263 nm             $E^{1\%}_{1cm} = 121$     $\epsilon = 6550$

EXAMPLE 7

Tert.-butyl cis 7-amino-3-ethyl-3-cepheme-4-carboxylate

STEP A: Tert.-butyl DL cis 7-amino-3-ethyl-3-cepheme-4-carboxylate 10 ml of methanol were added to a solution of 10.5 g of tert.-butyl DL cis 7-tritylamino-3-ethyl-3-cepheme-4-carboxylate in 20 ml of chloroform and after cooling slightly, 4 ml of an ethanolic solution of 10N hydrochloric acid were added thereto. The solution stood at room temperature for 10 minutes and was then vacuum filtered. The hydrochloride precipitate of the desired ester was washed with ether and dried. 3.5 g of the said hydrochloride were added to 15 ml of methylene chloride and 15 ml of aqueous saturated sodium bicarbonate solution with stirring and the organic phase was decanted. The aqueous phase was extracted with methylene chloride and the combined organic phases were dried over magnesium sulfate and evaporated to dryness to obtain 2.93 g of tert.-butyl DL cis 7-amino-3-ethyl-3-cepheme-4-carboxylate melting at 95°C. The product occurred in the form of colorless crystals soluble in methanol and ethanol, slightly soluble in ether and insoluble in water.

| Analysis: | $C_{13}H_{20}O_3N_2S$; | molecular weight = 284.31 | | |
|---|---|---|---|---|
| Calculated: | %C 54.92 | %H 7.09 | %N 9.85 | %S 11.25 |
| Found: | 55.1 | 7.0 | 9.8 | 11.4 |

I.R. Spectrum (chloroform): Presence of β-lactam at $1779^{cm-1}$, of conjugated ester at $1718^{cm-1}$ and NH at 3404 and $3333^{cm-1}$.

| U.V. Spectrum (ethanol): | |
|---|---|
| Inflex. towards 255 nm | $E^{1\%}_{1cm} = 207$ |
| Max. at 271 nm | $E^{1\%}_{1cm} = 231$   $\epsilon = 6600$ |
| Ethanol - N/10 HCl | |
| Max. at 257 nm | $E^{1\%}_{1cm} = 217$   $\epsilon = 6200$ |

STEP B: Resolution of Ester

A mixture of 2.84 g of tert.-butyl DL cis 7-amino-3-ethyl-3-cepheme-4-carboxylate, 1.65 g of D(-) tartaric acid and 8 ml of methanol was heated to 60°C and the temperature was returned to room temperature and held at 18°C for 10 minutes. The mixture was vacuum filtered and the precipitate was washed with a 1-1 methanol-ether mixture and then with ether and dried. The residue was then dissolved in 25ml of aqueous 10% sodium bicarbonate and 15 ml of methylene chloride and the organic phase was decanted. The aqueous phase was reextracted with methylene chloride and the combined organic phases were dried over magnesium sulfate and evaporate to dryness. The residue was taken up in ether and the mixture was vacuum filtered to obtain 1.19 g of the L (+) enantiomorph of tert.-butyl cis 7-amino-3-ethyl-3-cepheme-4-carboxylate melting at 120°C and having a specific rotation $[\alpha]_D^{20} = +74° ± 2.5°$ (c = 0.5% in chloroform).

The product occurred in the form of colorless crystals soluble in chloroform and insoluble in water. Concentration of the mother liquors and decomposition of the residual tartarate gave 1.02 g of the corresponding D (−) enantiomorph melting at 118°–120°C and having a specific rotation $[\alpha]_D^{20} = -67° ± 3$ ( c = 0.5% in chloroform).

EXAMPLE 8

DL cis 7-amino-3-ethyl-3-cepheme-4-carboxylic acid

A current of gaseous hydrochloric acid was passed through a mixture of 527 mg of tert.-butyl DL cis 7-tritylamino-3-ethyl-3-cepheme-4-carboxylate in 10 ml of nitromethane at 0°C for 15 minutes and the mixture was evaporated to dryness under reduced pressure. The residue was taken up in ether and the solution was vacuum filtered. The recovered precipitate was dissolved in one ml of water and pyridine was added to adjust the pH to 4. The mixture was vacuum filtered and the precipitate was washed with water, then acetone and ether and dried to obtain 185 mg of DL cis 7-amino-3-ethyl-3-cepheme-4-carboxylic acid melting above 250°C. The product occurred in the form of colorless crystals slightly soluble in water and ethanol and insoluble in ether and acetone.

| Analysis: | $C_9H_{12}O_3N_2S$; | molecular weight = 228.20 | | |
|---|---|---|---|---|
| Calculated: | %C 47.37 | %H 5.30 | 12.28 | %S 14.02 |
| Found: | 47.3 | 5.3 | 12.3 | 13.9 |

I.R. Spectrum (Nujol): Presence of β-lactam at $1798^{cm-1}$, C=C at $1647^{cm-1}$ and $COO^{(-)}$ at $1620^{cm-1}$.

| U.V. Spectrum (ethanol - N/10 HCl): | |
|---|---|
| Max. at 250–251 nm | $E^{1\%}_{1cm} = 247$   $\epsilon = 5600$ |
| Inflex. towards 65 nm | $E^{1\%}_{1cm} = 226$ |

EXAMPLE 9

Tert.-butyl cis 7-amino-3-isopropyl-3-cepheme-4-carboxylate

STEP A: Tert.-butyl DL cis 7-amino-3-isopropyl-3-cepheme-4-carboxylate

A solution of 7.57 g of tert.-butyl DL cis 7-tritylamino-3-isopropyl-3-cepheme-4-carboxylate in 14 ml of chloroform, 8.4 ml of methanol and 2.8 ml of ethanolic solution of 10N hydrochloric acid stood for 20 minutes and after the addition of 84 ml of ether, the mixture was vacuum filtered. The crystals recovered were washed with ether and dried to obtain 4.6 g of the hydrochloride of tert.-butyl DL cis 7-amino-3-isopropyl-3-cepheme-4-carboxylate. 3g of the said hydrochloride were added with stirring to 20 ml of methylene chloride and 25 ml of aqueous 10% sodium bicarbonate solution and after decanting the organic phase, the aqueous phase was extracted with methylene chloride. The organic phases were dried over magnesium sulfate and vacuum filtered. The filter was washed with methylene chloride and the filtrate was evaporated to dryness to obtain 2.54 g of tert.-butyl DL cis 7-amino-3-isopropyl-3-cepheme-4-carboxylate melting at 114°C. The product occurred in the form of colorless crystals soluble in alcohols, chloroform and ether and insoluble in water.

| Analysis: | $C_{14}H_{22}O_3N_2S$; | molecular weight = 298.41 | | |
|---|---|---|---|---|
| Calculated: | %C 56.36 | %H 7.43 | %N 9.39 | %S 10.73 |
| Found: | 56.1 | 7.3 | 9.3 | 10.4 |

I.R. Spectrum (chloroform): Presence of $NH_2$ 3404 and $3333^{cm-1}$, of β-lactam at $1773^{cm-1}$ and conjugated ester at $1721^{cm-1}$.

| U.V. Spectrum: | |
|---|---|
| Ethanol: Max. at 269 nm | $E^{1\%}_{1cm} = 236$   $\epsilon = 7050$ |
| Ethanol-N/10 HCl: max. at 258 | $E^{1\%}_{1cm} = 212$   $\epsilon = 6300$ |

STEP B: Resolution of Ester

A mixture of 2.38g of tert.-butyl DL cis 7-amino-3-isopropoyl-3-cepheme-4-carboxylate and 1.3 g of D (−) tartaric acid in 8 ml of methanol was heated to reflux and after cooling to 25°C, the mixture was vacuum filtered. The precipitate was washed with a 1-1 methanol-ether mixture and then with ether and dried to obtain 1.394 of the tartrate of tert.-butyl L (+) cis7-amino-3-isopropyl-3-cepheme-4-carboxylate.

The latter product was stirred with 15 ml of aqueous 10% sodium bicarbonate solution and 15 ml of methylene chloride and the organic phase was decanted. The aqueous phase was extracted with methylene chloride and the combined organic phases were dried over magnesium sulfate and evaporated to dryness to obtain 0.919 g of L (+) enantiomorph of tert.-butyl cis 7-amino-3-isopropyl-3-cepheme-4-carboxylate in the form of colorless crystals soluble in chloroform and insoluble in water. The product melted at 132°C and had a specific rotation $[\alpha]_D^{20} = +47.5° \pm 2.5°$ (c =0.6% in chloroform). Concentration of the mother liquors and decomposition of the residual tartrate gave 0.87 g of D (—) enantiomorph of the said ester melting at 120°C and having a specific rotation $[\alpha]_D^{20} = -35° \pm 2°$ (c = 1% in chloroform).

EXAMPLE 10

DL cis 7-amino-3-isopropyl-3-cepheme-4-carboxylic acid

A current of gaseous hydrogen chloride was passed for 15 minutes through a mixture of 541 mg of tert.-butyl DL cis 7-tritylamino-3-isopropyl-3-cepheme-4-carboxylate in 11 ml of nitromethane on an ice bath and the mixture was then evaporated to dryness. The residue was taken in ether and was vacuum filtered. The precipitate was washed with ether, dried and dissolved in 1 ml of water. The pH was adjusted to 4 with pyridine addition and the mixture was vacuum filtered. The crystals recovered were washed with water, then acetone and ether and dried to obtain 204mg of DL cis 7-amino-3-isopropyl-3-cepheme-4-carboxylic acid melting at 230°C with decomposition. The product occurred as colorless crystals slightly soluble in water, ethanol and acetone and insoluble in ether.

| Analysis: | $C_{10}H_{14}O_3N_2S$; | | molecular weight = 242.30 | |
|---|---|---|---|---|
| Calculated: | %C 59.58 | %H 5.83 | %N 11.57 | %S 13.20 |
| Found: | 49.3 | 5.9 | 11.5 | 13.4 |

I.R. Spectrum (Nujol): Presence of β-lactam at $1779^{cm-1}$, absorption region $COO^{(-)}$, C=C at 1642, 1623, 1543 and $1519^{cm-1}$.

| U.V. Spectrum: | | |
|---|---|---|
| Ethanol Inflex towards 245 nm | $E^{1\%}_{1cm} = 221$ | |
| Max at 267 nm | $E^{1\%}_{1cm} = 253$ | |
| Ethanol-N/10 HCl: Max. at 249 nm | $E^{1\%}_{1cm} = 222$ | $\epsilon = 5400$ |

EXAMPLE 11

L(+) cis 7-[D (—) α-aminophenylacetamido]-3-ethyl-3-cepheme-4-carboxylic acid STEP A: L(+) tert.-butyl cis 7-[D(—)-α-tert.-butoxycarbonamido-phenylacetamido]-3-ethyl-3-cepheme-4-carboxylate 1.65 g of dicyclohexylcarbodiimide were added to a cooled solution of 3.8 g of D (—) α-tert.-butoxycarbamidophenylacetic acid in 20 ml of chloroform and the mixture was stirred for 10 minutes. 1.13g of tert.-butyl L (+) cis 7-amino-3-ethyl-3-cepheme-4-carboxylate and 1 ml of pyridine were added thereto and the mixture was stirred for 5 hours at room temperature. The insolubles were removed by filtration and the filter was washed with ether. The ether filtrate was evaporated to dryness and the residue was taken up in 50 ml of ether. The mixture was vacuum filtered and the filtrate was washed with an aqueous 2N hydrochloric acid solution, with water, with a 10% sodium bicarbonate solution and with water. The solution was dried over magnesium sulfate and was evaporated to dryness under reduced pressure. The residue was empasted with 10 ml of isopropyl ether and 3 ml of ether and cooled and vacuum filtered. The residue was washed with isopropyl ether and dried to obtain 1.728 g of L (+) tert.-butyl cis 7-[D (—) α-tert.-butoxycarbonamidophenylacetamido]-3-ethyl-3-cepheme-4-carboxylate melting at 148°C.

STEP B: L (+) cis 7-[D (—) α-aminophenylacetamide]-3-ethyl-3-cepheme-4-carboxylic acid A solution of 1.55 g of the ester of Step A in 15 ml of trifluoroacetic acid stood at room temperature for 15 minutes and then was concentrated by ⅓ under reduced pressure at 30°C. 100 ml of isopropyl ether were added thereto and the mixture was stirred and vacuum filtered. The precipitate was washed with isopropyl ether and was then added to 10 ml of water. The mixture was filtered to remove insolubles and the filtrate pH was adjusted to 5 by pyridine addition. Crystallization was effected for 1 hour at room temperature and after cooling to 0°C, the mixture was vacuum filtered. The product was washed with water, with ethanol and then with ether to obtain 0.933 g of L (+) cis 7-[D (—) α-aminophenylacetamido]-3-ethyl-3-cepheme-4-carboxylic acid melting about 200°C with decomposition and having a specific rotation $[\alpha]_D^{20} = +109° \pm 3°$ (c = 0.5% in 0.1N hydrochloric acid). The product occurred as colorless crystals slightly soluble in water and ethanol and insoluble in ether.

| Analysis: | $C_{17}H_{19}O_4N_3S$; | | molecular weight = 361.40 | |
|---|---|---|---|---|
| Calculated: | %C 56.50 | %H 5.30 | %N 11.63 | %S 8.86 |
| Found: | 56.2 | 5.6 | 11.8 | 8.6 |

I.R. Spectrum (Nujol): Presence of conjugated COOH at $1693^{cm-1}$, of β-lactam and of secondary amide.

| U.V. Spectrum: | | |
|---|---|---|
| Ethanol: Max. at 263–264 nm | $E^{1\%}_{1cm} = 146$ | $\epsilon = 5300$ |
| Ethanol-N/10HCl: Max. at 257–258 nm | $E^{1\%}_{1cm} = 121$ | |

EXAMPLE 12

DL cis 7-p-nitrophenylacetamido-3-ethyl-3-cepheme-4-carboxylic acid

STEP A: Tert.-butyl DL cis 7-p-nitrophenylacetamido-3-ethyl-3-cepheme-4-carboxylate A suspension of 7.24 g of p-nitrophenylacetic acid and 4.5 g of dicyclohexylcarbodiimide in 50 ml of nitromethane and 10 ml of chloroform was stirred for 30 minutes at room temperature and was then vacuum filtered. The filter was washed with nitromethane containing 20% chloroform and 3.2 g the hydrochloride of tert.-butyl DL cis 7-amino-3-ethyl-3-cepheme-4-carboxylate and 5 ml of pyridine were added to the filtrate. The mixture stood at room temperature for 75 minutes and was then washed with N hydrochloric acid, then with water, dried over magnesium sulfate and evaporated to dryness. The residue was empasted with ether, vacuum filtered and dried to obtain 3.56 g of tert.-butyl DL cis 7-p-nitrophenylacetamido-3-ethyl-3-cepheme-4-carboxylate melting at 205°C. The wash water was made alkaline and the mother liquors were evporated to dryness to obtain a second crop of 0.18 g of the said product.

STEP B: DL cis 7-p-nitrophenylacetamido-3-ethyl-3-cepheme-4-carboxylic acid

A solution of 3.35 g of the ester of Step A in 33.5 ml of trifluoroacetic acid was stirred 10 minutes at room temperature and the solvent was distilled off under reduced pressure. The residue was empasted with benzene which was evaporated off under reduced pressure and the residue was then taken up in isopropyl ether. The mixture was vacuum filtered, washed with isopropyl ether and dried. The residue was dissolved in a 50—50 methanol-methylene chloride mixture and the insolubles were removed by vacuum filtration. The filtrate was concentrated and added to ether and vacuum filtered. The product recovered was washed with ether and dried to obtain 2.2 g of DL cis 7-p-nitrophenylacetamido-3-ethyl-3-cepheme-4-carboxylic acid melting above 230°C. The product occurred as colorless crystals soluble in pyridine, slightly soluble in alcohols and methylene chloride and insoluble in water and ether.

| Analysis: | $C_{17}H_{17}O_6N_3S$; | | molecular weight = 391.40 | |
|---|---|---|---|---|
| Calculated: | %C 52.17 | %H 4.38 | %N 10.74 | %S 8.18 |
| Found: | 51.9 | 4.2 | 10.5 | 7.8 |

I.R. Spectrum (Nujol): Presence of β-lactam at $1767^{cm-1}$, of amide at $1689^{cm-1}$ of secondary carbonyl doublet at 1664 and $1654^{cm-1}$ of C=C and of aromatic bands

| U.V. Spectrum: | | |
|---|---|---|
| Ethanol: Max. at 270 nm | $E^{1\%}_{1cm} = 435$ | $\epsilon = 17000$ |
| Ethanol-N/10HCl: Max at 270 nm | $E^{1\%}_{1cm} = 420$ | |

EXAMPLE 13

DL cis 7-p-aminophenylacetamido-3-ethyl-3-cepheme-4-carboxylic acid

A mixture of 900 mg of activated carbon and 2.8 ml of an aqueous solution of 2% palladium chloride and 27 ml of water was stirred and then a current of hydrogen was passed therethrough until 43 ml of hydrogen were absorped and the mixture was vacuum filtered. The palladized activated carbon was rinsed with water and was then used as the catalyst. The said palladized activated carbon was added to a solution of 900 mg of DL cis 7-p-nitrophenylacetamido-3-ethyl-3-cepheme-4-carboxylic acid in 7 ml of dimethylformamide and 2.5 ml of N hydrochloric acid and after purging with nitrogen, a current of hydrogen was passed therethrough until 169 ml of hydrogen were absorbed. The mixture was purged with nitrogen and then filtered to remove the catalyst. The filtrate was washed with a 50—50 water-ethanol mixture containing a few drops of hydrochloric acid and was evaporated to dryness. The residue was taken up in 8 ml of water and ammonium formate was added thereto to a pH of 3–4. The precipitate was recovered by vacuum filtration, was washed with water and dried under reduced pressure at 50°C to obtain 790 mg of DL cis 7-p-aminophenylacetamido-3-ethyl-3-cepheme-4-carboxylic acid melting above 230°C. The product occurred as ocre crystals slightly soluble in water and insoluble in ether.

| Analysis: | $C_{17}H_{19}O_4N_3S$; | | molecular weight = 361.42 | |
|---|---|---|---|---|
| Calculated: | %C 56.50 | %H 5.30 | %N 11.63 | %S 8.85 |
| Found: | 56.5 | 5.5 | 11.9 | 8.6 |

I.R. Spectrum (Nujol): Presence of β-lactam at $1773^{cm-1}$, of amide at $1661^{cm-1}$ and of aromatic bands.

| U.V. Spectrum (ethanol-N/10 HCl): | | |
|---|---|---|
| Max. at 256 nm | $E^{1\%}_{1cm} = 180$ | $\epsilon = 6500$ |
| Inflex. towards 266 nm | $E^{1\%}_{1cm} = 175$ | |

EXAMPLE 14

DL cis 7-(2'-thienyl)-acetamido-3-ethyl-3-cepheme-4-carboxylic acid

STEP A: Tert.-butyl DL cis 7-(2'-thienyl)-acetamido-3-ethyl-3-cepheme-4-carboxylate A solution of 970 mg of 2-theinylacetic acid chloride in 10 ml of methylene chloride was added under a nitrogen atmosphere to a cooled mixture of 1.60 g of the hydrochloride of tert.-butyl DL cis 7-amino-3-ethyl-3-cepheme-4-carboxylate with 32 ml of chloroform and 1.5 ml of pyridine and after standing 40 minutes at room temperature, the resulting solution was washed with a saturated sodium bicarbonate aqueous solution, then with N hydrochloric acid and with water. The solution was dried over magnesium sulfate and was evaporated to dryness. The residue was taken up in ether and was vacuum filtered. The solid product was washed with ether and dried to obtain 1.56 g of tert.-butyl DL cis 7-(2'-thienyl) acetamido-3-ethyl-3-cepheme-4-carboxylate melting at 125°C. Concentration of the mother liquor and crystallization from isopropyl ether gave a second crop of 250 mg of the said product.

STEP B. DL cis 7-(2'-thienyl)-acetamido-3-ethyl-3-cepheme-4-carboxylic acid

A solution of 816 mg of the ester of Step A in 8 ml of trifluoroacetic acid was stirred for 10 minutes and then evaporated to dryness. The residue was taken up in benzene and the solution was evaporated to dryness. The residue was empasted with ether, vacuum filtered, washed with ether and dried to obtain 576 mg of DL cis 7-(2'-thienyl)-acetamido-β-ethyl-3-cepheme-4-carboxylic acid melting above 230°C. The product occurred as colorless crystals soluble in pyridine, slightly soluble in ether and insoluble in water.

| Analysis: | $C_{15}H_{16}O_4N_2S_2$; | molecular weight = 352.43 |
|---|---|---|

-continued

| Calculated: | %C 51.14 | %H 4.58 | %N 7.95 | %S 18.17 |
|---|---|---|---|---|
| Found: | 51.4 | 4.7 | 7.6 | 18.0 |

I.R. Spectrum: Presence of β-lactam at $1779^{cm-1}$, of amide at $1642^{cm-1}$, of NH/OH at $3267^{cm-1}$ and of secondary amide at $1555^{cm-1}$.

| U.V. Spectrum (ethanol): | | |
|---|---|---|
| Max. at 238 nm | $E^{1\%}_{1cm} = 371$ | $\epsilon = 13,060$ |
| Inflex. towards 265 nm | $E^{1\%}_{1cm} = 186$ | |

EXAMPLE 15

DL cis 7-p-nitrophenylacetamido-3-isopropyl-3-cepheme-4-carboxylic acid

STEP A: Tert.-butyl DL cis 7-p-nitrophenylacetamido-3-isopropyl-3-cepheme-4-carboxylate A mixture of 3.78 g of p-nitrophenylacetic acid, 2.34 g of dicyclohexylcarbodiimide, 26 ml of nitromethane and 10.4 ml of chloroform was stirred under nitrogen for 20 minutes at room temperature and was vacuum filtered to remove insolubles. The filter was washed with a 1-1 nitromethanechloroform mixture and then 1.74 g of the hydrochloride of tert.-butyl DL cis 7-amino-3-isopropyl-3-cepheme-4-carboxylate and 2.1 ml of pyridine were added to the combined filtrates. After stirring for 1 hour under a nitrogen atmosphere, the mixture was vacuum filtered and the precipitate was washed with nitromethane, empasted with ether and dried to obtain 2.13 g of tert.-butyl DL cis 7-p-nitrophenylacetamido-3-isopropyl-3-cepheme-4-carboxylate melting at 250°C.

STEP B: DL cis 7-p-nitrophenylacetamido-3-isopropyl-3-cepheme-4-carboxylic acid A solution of 1.06 g of the ester of Step A in 10 ml of trifluoroacetic acid stood for 5 minutes and was then evaporated to dryness. The residue was taken up in benzene and evaporated to dryness. The residue was empasted with 20 ml of ether, stirred for 15 minutes, vacuum filtered, washed with ether and dried to obtain 790 mg of DL cis 7-p-nitrophenylacetamido-3-isopropyl-3-cepheme-4-carboxylic acid melting at 190°C with decomposition. The product occurred as colorless crystals slightly soluble in ethanol and insoluble in water.

| Analysis: | $C_{18}H_{19}O_6N_3S$; | molecular weight = 405.43 | | |
|---|---|---|---|---|
| Calculated: | %C 53.33 | %H 4.72 | %N 10.37 | %S 7.90 |
| Found: | 53.1 | 4.9 | 10.3 | 7.6 |

I.R. Spectrum (Nujol): Presence of β-lactam at $1772^{cm-1}$, of carbonyls at $1703^{cm-1}$ (acid) and $1656^{cm-1}$ (amide), of NH/OH at 3464 and $3276^{cm-1}$ and C=C bands.

U.V. Spectrum (ethanol): Max. at 268 nm $E^{1\%}_{1cm} = 405$ $\epsilon = 16,400$

EXAMPLE 16

DL cis 7-p-aminophenylacetamido-3-isopropyl-3-cepheme-4-carboxylic acid

A mixture of 400 mg of activated carbon, 2.8 ml of a solution of 2% palladium chloride in water and 12 ml of water was purged with nitrogen and then a hydrogen current was passed therethrough until saturated. The mixture was vacuum filtered and the resulting palladized activated carbon was rinsed with water.

The catalyst was added to a solution of 406 mg of DL cis 7-p-nitrophenylacetamido-3-isopropyl-3cepheme-4-carboxylic acid in 3.8 ml of dimethylformamide and 1.12 ml of N hydrochloric acid and a current of hydrogen was passed therethrough until saturated. The mixture was filtered and the filter was washed with a 50—50 water-ethanol solution containing a few drops of hydrochloric acid. The filtrate was evaporated to dryness and the residue was taken up in 3 ml of water. Ammonium formate was added thereto to a pH of 4.5 and the mixture was stirred 5 minutes and vacuum filtered. The precipitate was empasted with water and dried to obtain DL cis 7-p-aminophenylacetamido-3-isopropyl-3-cepheme-4-carboxylic acid melting at 150°C with decomposition. The product occurred as ocre crystals slightly soluble in water, ethanol and chloroform and insoluble in ether.

| Analysis: | $C_{18}H_{21}O_4N_3S$; | molecular weight = 375.45 | | |
|---|---|---|---|---|
| Calculated: | %C 57.59 | 5.64 | 11.20 | %S 8.53 |
| Found: | 57.3 | 5.8 | 11.3 | 8.3 |

I.R. Spectrum (Nujol): Presence of β-lactam at $1773^{cm-1}$, of amide at $1647^{cm-1}$, of secondary amide at $1533^{cm-1}$, of $COO^{(-)}$ at $1589^{cm-1}$ and absorptions in the OH/NH region.

| U.V. Spectrum | | |
|---|---|---|
| Ethanol: Max. at 244 nm | $E^{1\%}_{1cm} = 385$ | $\epsilon = 14,400$ |
| Inflex. towards 269 nm | $E^{1\%}_{1cm} = 188$ | |
| Ethanol-N/10HCl: Max. at 256 nm | $E^{1\%}_{1cm} = 161$ | $\epsilon = 6,000$ |

EXAMPLE 17

DL cis 7-(2'-thienyl)-acetamido-3-isopropyl-3-cepheme-4-carboxylic acid

2'A: TERT.-BUTYL DL cis 7-(2-thienyl)-acetamido-3-isopropyl-3-cepheme-4-carboxylate A solution of 386 mg 2-thienylacetic acid chloride in 2 ml of chloroform was added under nitrogen to a stirred cooled mixture of 670 mg of the hydrochloride of tert.-butyl DL cis 7-amino-3-isopropyl-3-cepheme-4-carboxylate, 6.7 ml of chloroform and 0.6 ml of pyridine and after standing for 10 minutes in the cold, the mixture stood at room temperature for ⅝⅞ minutes. The mixture was washed with N hydrochloric acid (pH 1) and the organic phase was decanted and washed with water. The aqueous phase was extracted with methylene chloride and the combined organic phases were added to 4 ml of 10% sodium bicarbonate dissolved in water. The mixture was stirred and the organic phase was decanted and washed with water. The aqueous phase was extracted with methylene chloride and the combined organic phases were dried over magnesium sulfate and evaporated to dryness. The residue was taken up in 15 ml of ether, stirred and vacuum filtered. The product was rinsed with ether and dried to obtain 624 mg of tert.-butyl DL cis 7-(2'-thienyl)-acetamido-3-isopropyl-3-cepheme-4-carboxylate melting at 170°C. Concentration of the mother liquor and crystallization of the residue from isopropyl ether gave a second crop of 120 mg of the product melting at 170°C.

STEP B: DL cis 7-(2'-thienyl)-acetamido-3-isopropyl-3-cepheme-4-carboxylic acid

A solution of 744 mg of the ester of Step A in 7.4 ml of trifluoroacetic acid stood for 5 minutes and was evaporated to dryness. The residue was taken up in benzene and was evaporated to dryness. The product was empasted with ether, vacuum filtered, washed with ether and dried to obtain 490 mg of DL cis 7-(2'-thienyl)-acetamido-3-isopropyl-3-cepheme-4-carboxylic acid melting above 200°C. The product occurred as colorless crystals soluble in methanol, slightly soluble in ethanol and insoluble in water.

| Analysis: | $C_{16}H_{18}O_4N_2S$; | molecular weight = 366.46 | | |
|---|---|---|---|---|
| Calculated: | %C 52.46 | %H 4.95 | %N 7.65 | %S 17.47 |
| Found: | 52.5 | 5.0 | 7.5 | 17.2 |

I.R. Spectrum (Nujol): Presence of β-lactam at $1776^{cm-1}$, of conjugated acid C=O at $1709^{cm-1}$, of amide at 1658 and $1645^{cm-1}$, of conjugated C=C at 1631 and $1550^{cm-1}$ and of secondary amide.

| U.V. Spectrum: | |
|---|---|
| Ethanol: Max. at 237–238 nm | $E^{1\%}_{1cm} = 367$ |
| Inflex. towards 263 nm | $E^{1\%}_{1cm} = 184$ |
| Ethanol-N/10HCl: Max. at 237–238 nm | $E^{1\%}_{1cm} = 368$ |
| Inflex. towards 263 nm | $E^{1\%}_{1cm} = 174$ |

EXAMPLE 18

L (+) cis 7-[D(−)-α-aminophenylacetamido]-3-isopropyl-3-cepheme-4-carboxylic acid STEP A: Tert.-butyl L(+) cis 7-[D(−)-α-tert.-butoxycarbamidophenylacetamido]-3-isopropyl-3-cepheme-4-carboxylate 0.895 g of tert.-butyl L(+) cis 7-amino-3-isopropyl-3-cepheme-4-carboxylate and 1 ml of pyridine were added to a solution of 3.01 g of D(−) α-tert.-butoxycarbamidophenylacetic acid in 20 ml of chloroform and 1.32 g of dicyclohexylcarbodiimide which had been cooled and stirred for 10 minutes and the mixture was then stirred for 4 hours. The insolubles were removed by filtration and the filtrate was washed with ether. The filtrate was evaporated to dryness and the residue was taken up in 20 ml of ether and filtered again. 30 ml of ether were added to the filtrate and the ether phase was washed with N hydrochloric acid, with water, with a 10% sodium bicarbonate in water solution and finally water. The filtrate was dried over magnesium sulfate and evaporated to dryness to obtain tert.-butyl L(+) cis 7-[D(−) α-tert.butoxycarbamidophenylacetamido]-3-isopropyl-3-cepheme-4-carboxylate.

STEP B: L(+) cis 7-[D(−)-α-aminophenylacetamido]-3-isopropyl -3-cepheme-4carboxylic acid A solution of the ester of Step A in 20 ml of trifluoroacetic acid stood for 15 minutes at room temperature and was evaporated to dryness under reduced pressure. The residue was taken up in benzene and evaporated to dryness and the residue was dissolved in 10 ml of water. Pyridine was added to adjust the pH to 6 and crystallization took place at room temperature for 15 minutes and then was cooled for 30 minutes. The mixture was vacuum filtered and the precipitate was washed with water, ethanol and then ether and dried. The product was dissolved in 6 ml of ethanol and 0.4 ml of triethylamine and the solution was vacuum filtered. The filter was washed with ethanol and 0.4 ml of acetic acid was added to the filtrate which was then filtered. The product was washed with ethanol, then with ether and dried to obtain 0.745 g of L(+) cis 7-[D(−)-α-aminophenylacetamido]-3-isopropyl-3-cepheme-4-carboxylic acid melting at 200°C with decomposition and had a specific rotation $[\alpha]_D^{20} = +90° \pm 3°$ (c = 0.5% in 0.1N hydrochloric acid). The product occurred as colorless crystals slightly soluble in ethanol and insoluble in ether.

| Analysis: | $C_{18}H_{21}O_4N_3S$; | molecular weight = 398.40 | | |
|---|---|---|---|---|
| Calculated: | %C 57.27 | %H 6.07 | %N 10.55 | %S 8.05 |
| Found: | 57.1 | 6.2 | 10.5 | 7.9 |

I.R. Spectrum (Nujol): Presence of conjugated COOH at $1693^{cm-1}$, of β-lactam and secondary amids.

U.V. Spectrum (ethanol): Max. at 258 nm $E_{1cm}^{1\%} = 157$ ∈ = 5900

EXAMPLE 19

L(+) 6R, 7R 7-[R(−) α-aminophenylacetamido]-3-cyclopentyl-3-cepheme-4-carboxylic acid STEP A: Tert.-butyl 3-cyclopentyl-2-oxo-3-butenoate A mixture of 12.3 g of cyclopentylmethyl ketone and 18.5 g of tert.-butyl dichloroacetate was cooled to −30°C with stirring under an inert atmosphere and a solution of 12.2 g of potassium tert.butylate in 60 ml of tetrahydrofuran was added thereto at the said temperature. After returning to room temperature, hexane and water were added and the organic phase was separated, washed with water and dried over magnesium sulfate. The solvents were evaporated off to leave an oily residue of tert.-butyl 2-chloro-3-cyclopentyl-2,3-epoxybutanoate. 26.5 g of the latter product were added to a solution of 3 g of lithium carbonate and 20 g of lithium bromide in 100 ml of hexamethylphosphorotriamide and after stirring for 1 hour at room temperature, petroleum ether and water were added thereto. The organic phase was washed with water, dried over magnesium sulfate and filtered. The solvent was evaporated to obtain an oily residue which was tert. butyl 3-cyclopentyl-2-oxo-3-butenoate which was used as is for the next step.

STEP B: Threo isomer of 2-(α-methoxycarbonyl-α-phthalimidomethyl)-4-tert.-butoxycarbonyl-5-cyclopentyl-4-hydroxy-1,3-thiazine 14 g of the hydrochloride of the thioaminal of methyl phthalimidomalonalaldehyde were added to a solution cooled at 0°C of 20 g of the product of Step A in 50 ml of ethanol and 6.3 ml of triethylamine were added dropwise thereto while keeping a 0°C temperature. The mixture was stirred at this temperature for 1 hour and was vacuum filtered. The recovered precipitate was washed with 50—50 ethanolwater solution, then with isopropyl ether and dried at 40°C under reduced pressure to obtain 11 g of the threo isomer of 2-($\alpha$-methoxycarbonyl-$\alpha$-phthalimidomethyl)-4-tert.-butoxycarbonyl-5-cyclopentyl-4hydroxy-1,3-thiazine melting at 140°C. The product occurred as colorless crystals soluble in methylene chloride and chloroform, slightly soluble in alcohol and ether and insoluble in water.

| Analysis: | $C_{25}H_{32}N_2O_7S$; | | molecular weight = 504.6 | |
|---|---|---|---|---|
| Calculated: | %C 59.51 | %H 6.39 | %N 5.55 | %S 6.35 |
| Found: | 59.3 | 6.4 | 5.3 | 6.6 |

I.R. Spectrum (chloroform): Presence of hydroxy at $3529^{cm-1}$, of phthalimido at 1782 and $1726^{cm-1}$, of conjugated ester at $1726^{cm-1}$ and ester in nitrogen at $1756^{cm-1}$.

STEP C: Threo isomer of 2-($\alpha$-methoxycarbonyl-$\alpha$-aminomethyl)-4-tertbutoxycarbonyl-5-cyclopentyl-2,3-dihydro-1,3-thiazine .HCl 86 g of the product of Step B were added to 95 ml of a solution of 2M hydrazine hydrate in dimethylformamide and after stirring for 1 hour at room temperature, 800 ml of ether containing 17 ml of acetic acid were added thereto. The mixture was stirred for 2 hours and vacuum filtered and the recovered precipitate was washed with ether. The combined organic phases were washed with aqueous solution saturated with sodium bicarbonate, then with water, dried over magnesium sulfate and slightly treated with an ethanolic solution of 10N hydrochloric acid. The precipitate formed was recovered by vacuum filtration and was then washed with ether and dissolved in 60 ml of warm methanol. 100 ml of ethyl ether and 200 ml of isopropyl ether were added thereto to precipitate and recover 29.6 g of the threo isomer of 2-($\alpha$-methoxycarbonyl-$\alpha$-aminomethyl)-4-tertbutoxycarbonyl-5-cyclopentyl-2,3-dihydro-1,3-thiazine hydrochloride melting at 150°C. The product occurred as colorless crystals soluble in methanol and ethanol, slightly soluble in ethyl acetate and insoluble in ether.

| Analysis: | $C_{17}H_{29}ClN_2O_4S$; | | molecular weight = 392.94 | | |
|---|---|---|---|---|---|
| Calculated: | %C 51.95 | %H 7.44 | %N 7.14 | %Cl 9.02 | %S 8.16 |
| Found: | 51.7 | 7.6 | 7.4 | 8.8 | 8.2 |

STEP D: 2-($\alpha$-carboxy-$\alpha$-aminomethyl)-4-tertbutoxycarbonyl-5-cyclopentyl-2,3-dihydro-1,3-thiazine 38 ml of 2N sodium hydroxide were added with stirring under a nitrogen atmosphere to a solution cooled to 0°C of 15.7 g of the hydrochloride of Step C in 80 ml of acetone and 16 ml of water and after stirring at 5°C for 10 minutes, carbon dioxide was bubbled therethrough for 20 minutes. The precipitate formed was recovered by vacuum filtration and was washed with water, with acetone and then with ether and dried at 40°C under reduced pressure to obtain 12 g of 2-($\alpha$-carboxy-$\alpha$-aminomethyl)-4-tertbutoxycarbonyl-5-cyclopentyl-2,3-dihydro-1,3-thiazine melting at 170°C. The product occurred as colorless crystals soluble in water, slightly soluble in ethanol and insoluble in ether.

| Analysis: | $C_{16}H_{26}N_2O_4S$; | | molecular weight = 342.46 | |
|---|---|---|---|---|
| Calculated: | %C 56.12 | %H 7.65 | %N 8.18 | %S 9.36 |
| Found: | 55.9 | 7.9 | 8.0 | 9.7 |

STEP E: Threo isomer of 2-($\alpha$-carboxy-$\alpha$-tritylaminomethyl)-4-tertbutoxycarbonyl-5-cyclopentyl-2,3-dihydro-1,3-thiazine 0.85 ml of triethylamine were added to a solution cooled to −55°C of 1.7 g of the product of Step D in 22 ml of chloroform and then a solution of 1.7 g of trityl chloride in 10 ml of chloroform was added dropwise. Another 0.85 ml of triethylamine was added and then the rest of trityl chloride solution. After standing at room temperature, the mixture was evaporated under reduced pressure and the residue was taken up in ether and water. The organic phase was decanted and was washed with dilute hydrochloric acid and water. The organic phase was dried over magnesium sulfate and evaporated under reduced pressure. The residue was triturated with isopropyl ether and crystallized. The residue was added to hexane and the crystals were recovered by vacuum filtration and were dried to obtain 1.5 g of the threo isomer of 2-($\alpha$-carboxy-$\alpha$-tritylaminomethyl)-4-tertbutoxycarbonyl-5-cyclopentyl-2,3-dihydro-1,3-thiazine melting at 190°C. The product occurred as colorless crystals soluble in chloroform, slightly soluble in methanol and ethanol and insoluble in water.

| Analysis: | $C_{35}H_{40}N_2O_4S$; | | molecular weight = 584.7 | |
|---|---|---|---|---|
| Calculated: | %C 71.89 | %H 6.90 | %N 4.79 | %S 5.48 |
| Found: | 72.2 | 6.8 | 4.5 | 5.4 |

STEP F: Tert.-butyl DL cis 7-tritylamino-3-cyclopentyl-3-cepheme-4-carboxylate 7.2 g of dicyclohexylcarbodiimide were added to a solution cooled to 5°C of 19.5 g of the product of Step E in 140 ml of chloroform and 600 ml of nitromethane and after stirring for 15 minutes, 12 ml of pyridine were added. The mixture was stirred overnight at room temperature and the insolubles were removed by vacuum filtration and were rinsed with ether. The filtrate was evaporated and the residue was taken up in 50 ml of methylene chloride and vacuum filtered. The filtrate was evaporated to dryness and the residue was taken up in ether and crystallization effected. The precipitate was recovered by vacuum filtration to obtain 13.1 g of tert.-butyl DL cis 7-tritylamino-3-cepheme-4-carboxylate melting at 210°C. The product occurred as colorless crystals soluble in methylene chloride and chloroform, slightly soluble in methanol, ethanol and ether and insoluble in water.

| Analysis: | $C_{35}H_{38}N_2O_3S$; | | molecular weight = 566.7 | |
|---|---|---|---|---|
| Calculated: | %C 74.18 | %H 6.76 | %N 4.94 | %S 5.65 |
| Found: | 74.0 | 7.1 | 4.7 | 5.5 |

STEP G: Tert.-butyl DL cis 7-amino-3-cyclopentyl-3-cepheme-4-carboxylate 2 ml of an ethanolic solution of 10N hydrochloric acid were added to a solution of 5.8 g of the product of Step F in 10 ml of chloroform and 6 ml of methanol and after standing 10 minutes at room temperature, the mixture was diluted with 60 ml of ether. The precipitate was vacuum filtered and washed with ether and added to an aqueous sodium bicarbonate solution. The mixture was extracted with methylene chloride and the organic phase was dried and concentrated to dryness. The residue was added to isopropyl ether and the crystals obtained by vacuum filtration were washed with hexane to obtain 3.1 g of tert.-butyl DL cis 7-amino-3-cyclopentyl-3-cepheme-4-carboxylate melting at 150°C. The product occurred as colorless crystals soluble in isopropyl ether and insoluble in water and hexane.

| Analysis: | $C_{16}H_{24}N_2O_3S$; | | molecular weight = 324.45 | |
|---|---|---|---|---|
| Calculated: | %C 59.24 | %H 7.46 | %N 8.64 | 9.86 |
| Found: | 59.4 | 7.7 | 8.5 | 9.6 |

STEP H: DL cis 7-amino-3-cyclopentyl-3-cepheme-4-carboxylic acid

A current of gaseous hydrogen chloride was passed through a mixture of 585 mg of the product of Step G and 12 ml of nitromethane cooled to 0°C for 15 minutes and the mixture was evaporated to dryness under reduced pressure. The residue was taken up in ether and the crystals were recovered by vacuum filtration. The residue was dissolved in 2 ml of ethanol and 1 ml of water and pyridine was added to a pH of 4. The mixture was agitated until crystallization appeared and the crystals were recovered by vacuum filtration, were rinsed with ethanol and dried to obtain 249 mg of DL cis 7-amino-3-cyclopentyl-3-cepheme-4-carboxylic acid melting at 250°C. The product occurred as colorless crystals slightly soluble in ethanol and insoluble in water and ether.

| Analysis: | $C_{12}H_{16}N_2O_3S$; | | molecular weight = 268.34 | |
|---|---|---|---|---|
| Calculated: | %C 53.72 | %H 6.01 | %N 10.44 | %S 11.93 |
| Found: | 53.5 | 5.9 | 10.7 | 11.9 |

STEP I: L(+) 6R, 7R 7-[R(−)) α-aminophenylacetamido]-3-cyclopentyl-3-cepheme-4-carboxylic acid 1.3 g of dicyclohexylcarbodiimide were added with stirring to a solution cooled to 5°C of 3 g of R (−) α-tert.-butoxycarbamidophenyl acetic acid in 20 ml of chloroform and after stirring the mixture for 10 minutes, 0.5 ml of pyridine and 1.6 g of the product of Step G were added thereto. The mixture was stirred for 1 hour at room temperature and was vacuum filtered. The filtrate was evaporated to dryness and the residue was taken up in a 4–1 ethyl acetate-methylene chloride mixture. The organic solution was washed with water and aqueous sodium bicarbonate solution, dried over magnesium sulfate and evaporated to dryness. The residue was triturated with isopropyl ether to obtain 2.7 g of colorless crystals of tert.-butyl 7-[R (−) α-tert-butoxycarbamidophenyl acetamido]-3-cyclopentyl-3-cepheme-4-carboxylate diastereoismers.

The said crystals were suspended in 25 ml of ether and the crystals were vacuum filtered and dried to obtain 1.3 g of product melting at 185°C. The ether filtrate was evaporated to dryness and the residue was disintegrated in hexane to obtain 1.2 g of product melting at 125°C and 1 g of this product was dissolved in 10 ml of trifluoroacetic acid. The solution stood for 1 hour at room temperature and was then evaporated to dryness under reduced pressure. The residue was added to 20 ml of isopropyl ether and the crystals formed were recovered by vacuum filtration and stirred with water containing pyridine. The crystals were vacuum filtered and crystallized from 50—50 ethanol-water solution to obtain 495 mg of L(+) 6R, 7R 7-[R(−)-α-aminophenylacetamide]-3-cyclopentyl-3-cepheme-4-carboxylic acid melting at 200°C with decomposition and having a specific rotation $[\alpha]_D^{20} = +82 \pm 3°$ (c = 0.5% in 0.1N hydrochloric acid). The product occurred as colorless crystals slightly soluble in water and ethanol and insoluble in ether.

| Analysis: | $C_{20}H_{23}N_3O_4S$; | | molecular weight = 401.5 | |
|---|---|---|---|---|
| Calculated: | %C 59.84 | %H 5.78 | %N 10.46 | %S 7.99 |
| Found: | 59.9 | 5.7 | 10.8 | 7.9 |

EXAMPLE 20

DL cis 7-p-nitrophenylacetamido-3-cyclopentyl-3-cepheme-4-carboxylic acid

STEP A: Tert.-butyl DL cis 7-p-nitrophenylacetamido-3-cyclopentyl-3-cepheme-4-carboxylate A mixture of 1.45 g of p-nitrophenylacetic acid and 880 mg of dicyclohexylcarbodiimide, 10 ml of nitromethane and 4 ml of chloroform was stirred under nitrogen and after standing at room temperature for 45 minutes, the insolubles were removed by vacuum filtration and rinsed with chloroform. 650 mg of the product of Step G of Example 19 were added to the combined filtrates and after the addition of 0.8 ml of pyridine, the mixture was stirred under a nitrogen atmosphere for 1½ hours. The organic solution was treated with aqueous N hydrochloric acid, then with aqueous sodium bicarbonate solution and then water, dried over magnesium sulfate and evaporated to dryness. The residue was taken up in ether and the crystals formed were vacuum filtered and rinsed with ether and dried to obtain 905 mg of tert.-butyl DL cis 7-p-nitrophenylacetamido-3-cyclopentyl-3-cepheme-4-carboxylate in the form of colorless crystals.

STEP B: DL cis 7-p-nitrophenylacetamido-3-cyclopentyl-3-cepheme-4-carboxylic acid A solution of 244 mg of the ester of Step A in 2.5 ml of trifluoroacetic acid stood at room temperature for 8 minutes and was then evaporated to dryness under reduced pressure. The residue was taken up in benzene and was evaporated to dryness. The residue was triturated with ether and crystallization was effected. The crystals were vacuum filtered, washed with ether and dried to obtain 174 mg of DL cis 7-p-nitrophenylacetamido-3-cyclopentyl-3-cepheme-4-carboxylic acid melting at 170°C. The product occurred as colorless crystals slightly soluble in ethanol and insoluble in ether and water.

| Analysis: | $C_{20}H_{21}N_3O_6S$; | | molecular weight = 431.47 | |
|---|---|---|---|---|
| Calculated: | %C 55.68 | %H 4.91 | %N 9.74 | %S 7.42 |
| Found: | 55.5 | 5.2 | 9.6 | 7.3 |

EXAMPLE 21

DL cis 7-aminophenylacetamido-3-cyclopentyl-3-cepheme-4-carboxylic acid

A mixture of 900 mg of activated carbon, 2.8 ml of 2% palladium chloride aqueous solution and 27 ml of water was stirred and a current of hydrogen was bubbled therethrough until 43 ml of hydrogen were absorbed. The mixture was vacuum filtered and the palladized activated carbon was rinsed with water. The said carbon was added to a solution of 900 mg of DL cis 7-p-nitrophenylacetamido-3-cyclopentyl-3-cepheme-4-carboxylic acid in 7 ml of dimethylformamide and 2.5 ml of N hydrochloric acid and after purging with nitrogen, a current of hydrogen was passed therethrough with stirring. The catalyst was filtered off and the filtrate was evaporated to dryness. The residue was added to water and ammonium formate was added thereto and the crystals were vacuum filtered and dried at 50°C to obtain DL cis 7-p-aminophenylacetamido-3-cyclopentyl-3-cepheme-4-carboxylic acid as colorless crystals soluble in ethanol, slightly soluble in water and insoluble in ether.

EXAMPLE 22

DL cis 7-(2'-thienyl)-acetamido-3-cyclopentyl-3-cepheme-4-carboxylic acid

STEP A: Tert-butyl DL cis 7-(2'-thienyl)-acetamido-3-cyclopentyl-3-cepheme-4-carboxylate.

Using the procedure of Step A of Example 20, 1.14 g of 2-thienylacetic acid were reacted to obtain 810 mg of tert.-butyl DL cis 7-(2'-thienyl)-acetamido-3-cyclopentyl-3-cepheme-4-carboxylate in the form of colorless crystals.

STEP B:

Using the procedure of Step B of Example 20, 225 mg of tert.-butyl DL cis 7-(2'-thienyl)-acetamido-3-cyclopentyl-3-cepheme-4-carboxylate were reacted to obtain 130 mg of DL cis 7-(2'-thienyl)-acetamido-3-cyclopentyl-3-cepheme-4-carboxylic acid melting at 220°C. The product occurred as colorless crystals slightly soluble in water and insoluble in ether.

| Analysis: | $C_{18}H_{20}N_2O_4S$; | | molecular weight = 392.50 | |
|---|---|---|---|---|
| Calculated: | %C 55.10 | %H 5.14 | %N 7.14 | %S 16.31 |
| Found: | 55.0 | 5.2 | 7.1 | 16.1 |

PHARMACOLOGICAL STUDY

The antibiotic activity was determined by the diffusion method in a gelose medium at a pH of 7. The following Table expresses the mineral concentration of inhibition in mcg/ml (CM1) for the products against different microbial strains.

TABLE I

| Products | Staph. aureus oxford U.C. 1061 P(+) | Staph. U.C. 1128 P(−) | Strept. hemoly. Todd Hewitt | Strept. Fecalis 5432 | Bac. Subt. | Escher. Coli UC 1020 | Escher. Coli UC 1261 | Pseudomonas |
|---|---|---|---|---|---|---|---|---|
| DL cis 7-(2'-thienyl)-acetamido-3-ethyl-3-cepheme-4-carboxylic acid | 3 | 10 | 20 | >40 | 0.4 | >200 | 200 | >200 |
| DL cis 7-p-aminophenylacetamido-3-ethyl-3-cepheme-4-carboxylic acid | 5 | 10 | >40 | 40 | 0.4 | >200 | >200 | >200 |
| L(+) cis 7-(D(−) α-aminophenylacetamino)-3-ethyl-3-cepheme-4-carboxylic acid | 1 | 3 | 20 | 40 | 0.1 | 20 | 20 | >200 |
| DL cis 7-p-nitrophenylacetamido-3-ethyl-3-cepheme-4-carboxylic acid | 3 | 5 | 10 | >40 | 1 | >200 | >200 | >200 |
| DL cis 7-(2'-thienly)acetamido-3-isopropyl-3-cepheme-4-carboxylic acid | 2 | 5 | 10 | >40 | 0.4 | >200 | >200 | >200 |
| DL cis 7-p-nitrophenylacetamido-3-isopropyl-3-cepheme-4-carboxylic acid | 0.4 | 2 | 5 | >40 | 0.2 | >200 | >200 | >200 |
| DL cis 7-p-aminophenylacetamido-3-isopropyl-3-cepheme-4-carboxylic acid | 2 | 10 | 10 | >40 | 0.05 | >200 | >200 | >200 |
| L(+) cis 7-(D(−)α-aminophenylacetamido)-3-isopropyl-3-cepheme-4-carboxylic acid | 0.4 | 2 | 10 | 20 | 0.2 | 100 | 40–100 | >100 |
| DL cis 7-p-nitro- | | | | | | | | |

TABLE I-continued

| Products | Staph. aureus oxford U.C. 1061 P(+) | Staph. U.C. 1128 P(−) | Strept. hemoly. Todd Hewitt | Strept. Fecalis 5432 | Bac. Subt. | Escher. Coli UC 1020 | Escher. Coli UC 1261 | Pseudo-monas |
|---|---|---|---|---|---|---|---|---|
| phenylacetamido-3-cyclopentyl-3-cepheme-4-carboxylic acid | 0.2 | 0.4 | >40 | >40 | 0.1 | | | |
| L(+) 6R, 7R 7-[R(−) α-amino phenylacetamido] 3-cyclopentyl-3-cepheme-4-carboxylic acid | 0.4 | 1 | 10 | 20 | 0.05 | | | |
| DL cis 7-(2'-thienyl)acetamido-3-cyclopentyl-3-cepheme-4-carboxylic acid | 1 | 1 | >40 | 20 | 1 | | | |
| Cephalexin | 2 | 10 | 10 | 60 | 0.2 | 20 | 20 | |

P(+) - penicillin sensitive
P(−) - penicillin resistant

Table I shows that the compounds of the invention possess a good activity against pathogenic microorganisms, particularly against staphylococcus.

L(+) cis 7-[D(−) α-aminophenylacetamido]-3-ethyl-3-cepheme-4-carboxylic acid (compound A) was tested on groups of 15 mice infected with 0.3 ml of a culture of Escherichia Coli. $T_{26}B_6$ administered intraperitoneally. Compound A and Cephalexin were orally administered to the mice 1 and 5 hours after the infection and after 48 hours, the number of mice surviving was determined. The results are reported in Table II.

TABLE II

| | Oral dose in mg/kg | % Surviving after 1 day | 2 days |
|---|---|---|---|
| Control | 0 | 0 | |
| Compound A | 2 × 150 | 33 | 7 |
| | 2 × 250 | 73 | 7 |
| Cephalexin | 2 × 150 | 13 | 0 |
| | 2 × 250 | 26 | 0 |

Table II shows that compound A has a notable oral antibacterial activity against severe infections of colibacilli and notably retards mortality in mice so infected.

In another test, it was determined that the concentration of compound A in the blood is more durable than Cephalexin and is therefore more efficacious. In effect, the practical plasmatic doses in the rat is made clear by particularly remarkable oral absorption and a relatively slow disappearance of the antibactic. This was shown by measuring the plasmatic ratio in rats after a single administration of a does of 50 mg/kg orally of compound A and Cephalexin. The results are reported in Table III.

TABLE III

| | Time in hours | Plasmatic ratio mcg/ml |
|---|---|---|
| Compound A | 1 | 21 |
| | 2 | 15 |
| | 4 | 6 |
| Cephalexin | 1 | 17 |
| | 2 | 8 |
| | 4 | 4 |

Various modification of the compositions and method of the invention may be made without departing from the spirit or scope thereof and it should be understood that the invention is to be limited only as defined in the appended claims.

We claim:

1. A compound of the formula

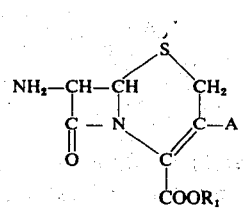

wherein A is selected from the group consisting of alkyl of 2 to 5 carbon atoms and cycloakyl of 3 to 7 carbon atoms and $R_1$ is selected from the group consisting of hydrogen, alkyl of 1 to 6 carbon atoms, trichloroethyl, benzyl and methoxybenzyl.

2. A compound selected from the group consisting of racemates and optically active isomers of cis and trans isomers and mixtures thereof of a compound of the formula

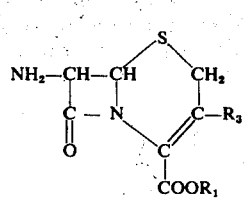

wherein $R_3$ is alkyl of 2 to 5 carbon atoms and $R_1$ is selected from the group consisting of hydrogen, alkyl of 1 to 6 carbon atoms, trichloroethyl, benzyl and methoxybenzyl.

3. A compound selected from the group consisting of cis and trans isomers and mixtures thereof and racemates and optically active isomers of a compound of the formula

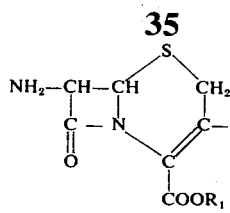
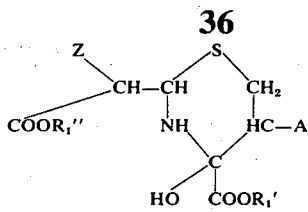

wherein $R_1$ is selected from the group consisting of hydrogen, alkyl of 1 to 6 carbon atoms, trichloroethyl, benzyl and methoxybenzyl and A' is cycloalkyl of 3 to 7 carbon atoms.

4. A process for the preparation of a compound of the formula

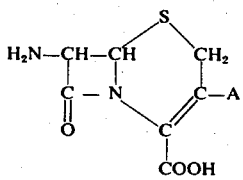

wherein A is selected from the group consisting of alkyl of 2 to 5 carbon atoms and cycloalkyl of 3 to 7 carbon atoms comprising the steps of reacting a compound of the formula

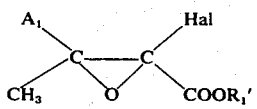

III wherein $A_1$ is A, $R'_1$ is selected from the group consisting of alkyl of 1 to 6 carbon atoms, trichloroethyl, benzyl and methoxybenzyl and Hal is selected from the group consisting of chlorine and bromine with a dehydrohalogenating consisting of chlorine and bromine with a dehydrohalogenating agent to form a ester of an α-methylene-α-oxo-carboxylic acid of the formula

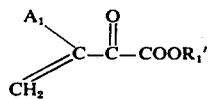

IV reacting the said ester, $A_1$ being A, in the presence of a weakly basic tertiary amine with a threo isomer, erythro isomer or mixtures thereof of a thioaminal of the formula

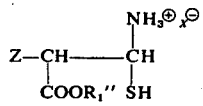

V wherein Z is selected from the group consisting of optionally substituted cyclic imido, benzoylamino and thiobenzoylamino, $R''_1$ is alkyl of 1 to 10 carbon atoms and $X^-$ is an anion selected from the group consisting of halogen, an anion of sulfuric acid and an anion of sulfonic acid to either form a 1,3-thiazine of the formula existing in threo or erythro form or a mixture thereof, subjecting the latter to hydrogenolysis or hydrazine treatment and then to an acid to obtain a 2,3-dihydro-1,3-thiazine of the formula

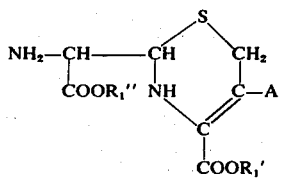

VII or to form a 1,3-thiazine of the formula

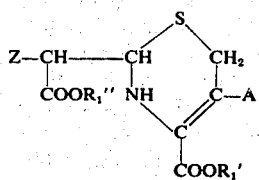

VI' existing in threo or erythro form or mixtures thereof, subjecting the latter to hydrazine or hydrogenolysis to obtain the compound of formula VII, subjecting the latter to selective saponification with a basic agent to obtain a compound of the formula

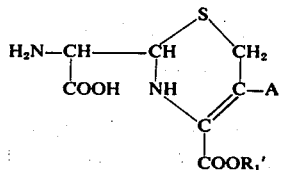

VIII in its threo or erythro form or a mixture thereof, reacting the latter with trityl chloride to form a 2,3-dihydro-1,3-thiazine of the formula

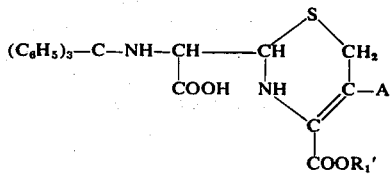

IX in its threo or erythro form or mixtures thereof, subjecting the latter to cyclization with a lactamization agent selected from the group consisting of dialkylcarbodiimides and dicycloalkylcarbodiimides to form a compound of the formula

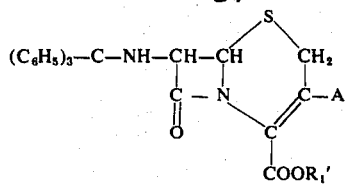　　　　　　　　　　　　X in its cis or trans form or mixtures thereof and either reacting the latter with an acid under mild conditions to form a compound of the formula

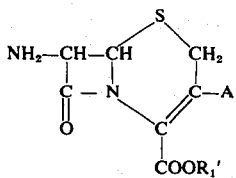　　　　　　　　　　　　XI in its cis or trans form and mixtures thereof or reacting the compound of formula IX with an acid agent under severe conditions to form a compound of the formula

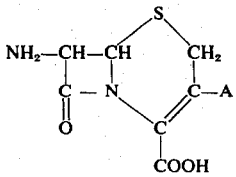　　　　　　　　　　　　XIa in its cis or trans form or mixtures thereof.

5. The process of claim 4 wherein the compound of formula XI is subjected to a process selected from the group consisting of acid hydrolysis and acid hydrogenolysis to form the corresponding free acid.

6. A process for the preparation of a compound of the formula

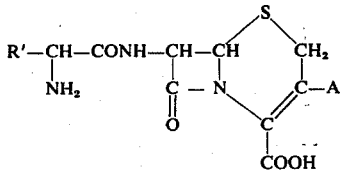

in its cis or trans form or mixtures thereof and racemates and optically active isomers thereof wherein R' is selected from the group consisting of phenyl optionally substituted with up to two members of the group consisting of halogen and nitro and thienyl and pyridyl and A is selected from the group consisting of alkyl of 2 to 5 carbon atoms and cycloalkyl of 3 to 7 carbon atoms comprising subjecting a compound of the formula

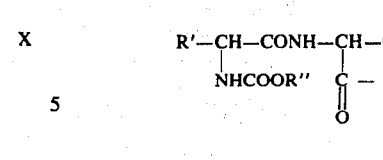

wherein $R_1$ has the definition in claim 1 and R'' is alkyl of 1 to 5 carbon atoms to process selected from the group consisting of hydrogenolysis and acid hydrolysis.

7. The process of claim 4 wherein a compound selected from the group consisting of compounds of formula XI and XIa is reacted with an acylating derivative of an acid of the formula

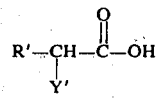

wherein R' is selected from the group consisting of phenyl optionally substituted with up to two members of the group consisting of halogen and nitro and of a thienyl and pyridyl group and Y' is selected from the group consisting of hydrogen, hydroxy and NHCOOR'' and R'' is alkyl of 1 to 5 carbon atoms.

8. The process of claim 4 wherein a compound of formula

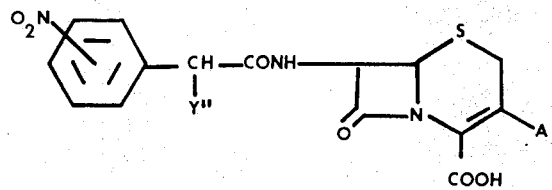

wherein Y'' is selected from the group consisting of hydrogen and hydroxy, is reacted with a reducing agent to form a compound of formula

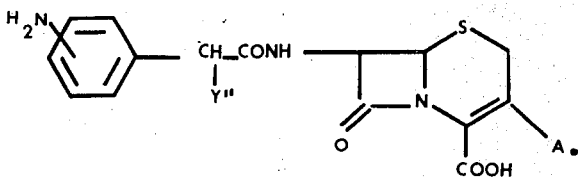

* * * * *

UNITED STATES PATENT OFFICE
CERTIFICATE OF CORRECTION

Patent No. 3,962,223          Dated June 8, 1976

Inventor(s) JACQUES MARTEL and RENE HEYMES

It is certified that error appears in the above-identified patent and that said Letters Patent are hereby corrected as shown below:

| Col. | Line | |
|---|---|---|
| [30] | | Priority Date "Dec. 31, 1971" should be --Sept. 7, 1972-- |
| 1 | 20 | Please insert --THE INVENTION-- |
| 7 | 30 | Formula XV |

"$R^1CH-CONH-CH-CH$
   $|$
   $NHCOOR"$

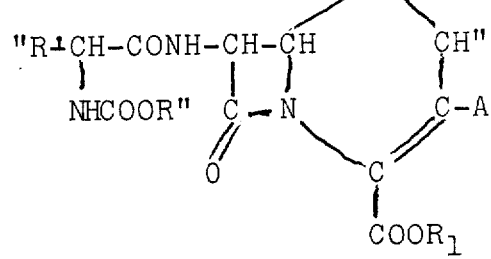

should be

--$R^1CH-CONH-CH-CH$
   $|$
   $NHCOOR"$

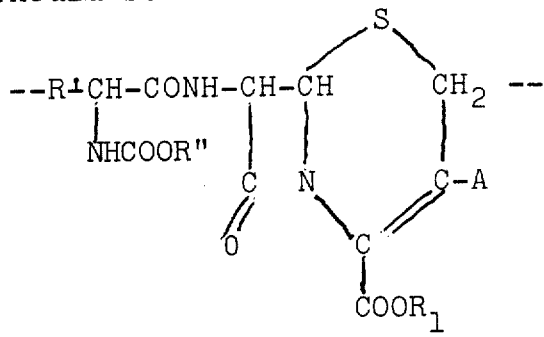

--

UNITED STATES PATENT OFFICE
CERTIFICATE OF CORRECTION Page 2 of 3

Patent No. 3,962,223  Dated June 8, 1976

Inventor(s) JACQUES MARTEL and RENE HEYMES

It is certified that error appears in the above-identified patent and that said Letters Patent are hereby corrected as shown below:

| Col. | Line | |
|------|------|---|
| 12 | 29 | "2,3dihy" should be --2,3-dihy-- |
| 12 | 58&59 | "2(α-carboxy⍺" should be --2(α-carboxy-α-- |
| 14 | 14 | "1679$^{cm-\cdot}$" should be --1679$^{cm-1}$-- |
| 16 | 8 | "dl" should be --DL-- |
| 19 | 43 | First Col. "59.58" should be --49.58-- |
| 22 | 37 | "theinylacetic" should be --thienylacetic-- |
| 24 | 53 | "2'A" should be --Step A-- |
| 24 | 61 | "5/8 7/8" should be --45-- |
| 27 | 6 | "ethanolwater" should be --ethanol-water-- |
| 27 | 10 | "4hydroxy" should be --4-hydroxy-- |

UNITED STATES PATENT OFFICE
CERTIFICATE OF CORRECTION Page 3 of 3

Patent No. 3,962,223   Dated June 8, 1976

Inventor(s) JACQUES MARTEL and RENE HEYMES

It is certified that error appears in the above-identified patent and that said Letters Patent are hereby corrected as shown below:

| Col. | Line | |
|---|---|---|
| 29 | 45 | Cancel one ")" |
| Claim 4 35 | 38&39 | Cancel one "with a dehydrohalogenating consisting of chlorine & bromine" |

" "   Formula V   " $Z-\underset{\underset{COOR_1''}{|}}{CH}-\underset{\underset{SH}{|}}{\overset{\overset{NH_3 \oplus \quad X \ominus}{|}}{CH}}$ "   should be -- $-Z-\underset{\underset{COOR_1''}{|}}{CH}-\underset{\underset{SH}{|}}{\overset{\overset{NH_3 \oplus \quad X \ominus}{|}}{CH}}$ --

Signed and Sealed this

Fifteenth Day of February 1977

[SEAL]

Attest:

RUTH C. MASON
Attesting Officer

C. MARSHALL DANN
Commissioner of Patents and Trademarks